United States Patent
Paterson et al.

(10) Patent No.: US 11,432,935 B2
(45) Date of Patent: Sep. 6, 2022

(54) ORTHOPAEDIC IMPLANTS INCLUDING PERIPHERAL APERTURE ARRANGEMENTS

(71) Applicant: Arthrex, Inc., Naples, FL (US)

(72) Inventors: John D. Paterson, Naples, FL (US); Rudraksh Khosla, Naples, FL (US)

(73) Assignee: ARTHREX, INC., Naples, FL (US)

( * ) Notice: Subject to any disclaimer, the term of this patent is extended or adjusted under 35 U.S.C. 154(b) by 0 days.

(21) Appl. No.: 16/837,201

(22) Filed: Apr. 1, 2020

(65) Prior Publication Data

US 2021/0307919 A1    Oct. 7, 2021

(51) Int. Cl.
  *A61F 2/40*    (2006.01)
  *A61F 2/30*    (2006.01)

(52) U.S. Cl.
  CPC ........ *A61F 2/4081* (2013.01); *A61F 2/30734* (2013.01); *A61F 2/30771* (2013.01); *A61F 2002/30736* (2013.01); *A61F 2002/30784* (2013.01); *A61F 2002/4085* (2013.01)

(58) Field of Classification Search
  CPC .. A61F 2002/30405; A61F 2002/30578; A61F 2002/30772; A61F 2002/30827; A61F 2002/3093; A61F 2/28; A61F 2/3609; A61F 2002/30242; A61F 2002/3611; A61F 2002/3625; A61F 2/3859; A61F 2/4014; A61F 2/4081; A61F 2/4612; A61F 2/4618; A61F 2002/2853; A61F 2002/30115; A61F 2002/30126; A61F 2002/30266; A61F 2002/30281; A61F 2/30734; A61F 2/30771; A61F 2002/30736; A61F 2002/4085; A61F 2002/30784; A61B 17/1764; A61B 17/0401; A61B 17/3468; A61B 2017/564; A61B 17/157; A61B 17/1739; A61B 17/8061; A61B 2034/102; A61B 17/86; A61B 17/1684; A61B 17/1778; A61B 2017/044; A61B 17/1664; A61B 17/1668; A61B 17/1675; A61B 17/1677; A61B 17/1682; A61B 17/1721; A61B 17/1742
  See application file for complete search history.

(56) References Cited

U.S. PATENT DOCUMENTS

| | | | | |
|---|---|---|---|---|
| 8,070,820 B2 * | 12/2011 | Winslow | ............... | A61F 2/4014 623/19.12 |
| 8,303,665 B2 * | 11/2012 | Tornier | ............... | A61F 2/30734 623/19.11 |
| 8,632,597 B2 | 1/2014 | Lappin | | |
| 8,852,283 B2 | 10/2014 | Tornier et al. | | |
| 8,940,054 B2 * | 1/2015 | Wiley | ................ | A61F 2/30734 623/19.13 |

(Continued)

OTHER PUBLICATIONS

Musculoskeletal Key. Arthrex Univers Revers (TM) shoulder prosthesis. Retrieve from: https://musculoskeletalkey.com/arthrex-univers-revers-shoulder-prosthesis/.

*Primary Examiner* — Ann Schillinger
(74) *Attorney, Agent, or Firm* — Carlson, Gaskey & Olds, P.C.

(57) ABSTRACT

This disclosure relates to orthopaedic implants and methods for repairing bone defects and restoring functionality to a joint. The implants disclosed herein include augment geometries that may approximate a surface contour or bone void along a surgical site and include patterns of peripheral apertures that may be utilized for improved fixation of the implants at the surgical site.

25 Claims, 14 Drawing Sheets

(56) References Cited

U.S. PATENT DOCUMENTS

| | | |
|---|---|---|
| 9,114,017 B2 | 8/2015 | Lappin |
| 9,226,830 B2 * | 1/2016 | De Wilde .......... A61B 17/1778 |
| 9,233,003 B2 | 1/2016 | Rouche et al. |
| 9,283,083 B2 | 3/2016 | Winslow et al. |
| 9,452,055 B2 | 9/2016 | Lappin |
| 9,532,880 B2 | 1/2017 | Lappin |
| 9,545,312 B2 | 1/2017 | Tornier et al. |
| 9,629,725 B2 | 4/2017 | Gargac et al. |
| 9,844,440 B2 | 12/2017 | Kovacs et al. |
| 10,034,757 B2 | 7/2018 | Kovacs et al. |
| 10,265,184 B2 | 4/2019 | Lappin |
| 10,357,373 B2 | 7/2019 | Gargac et al. |
| 10,383,735 B2 | 8/2019 | Wiley et al. |
| 10,813,769 B2 * | 10/2020 | Orphanos ............. A61F 2/4014 |
| 10,856,994 B1 * | 12/2020 | Hodorek ............... A61F 2/4081 |
| 2003/0114933 A1 * | 6/2003 | Bouttens ............... A61F 2/4081 623/19.13 |
| 2003/0158605 A1 * | 8/2003 | Tornier .................... A61F 2/40 623/19.11 |
| 2013/0150973 A1 * | 6/2013 | Splieth .................. A61F 2/4081 623/19.11 |
| 2013/0261751 A1 * | 10/2013 | Lappin .................. A61F 2/4081 623/19.11 |
| 2014/0243986 A1 * | 8/2014 | Frankle .................... A61F 2/40 623/19.12 |
| 2015/0305877 A1 * | 10/2015 | Gargac .................. A61F 2/4081 623/19.11 |
| 2016/0045323 A1 * | 2/2016 | Kovacs ............... A61F 2/30734 623/19.11 |
| 2017/0095336 A1 | 4/2017 | Tornier et al. |
| 2018/0303618 A1 | 10/2018 | Kovacs et al. |
| 2018/0333268 A1 | 11/2018 | Cardon et al. |
| 2019/0015116 A1 | 1/2019 | Gargac et al. |
| 2019/0015117 A1 | 1/2019 | Neichel et al. |
| 2019/0015118 A1 | 1/2019 | Neichel et al. |
| 2019/0015221 A1 | 1/2019 | Neichel et al. |
| 2019/0151106 A1 | 5/2019 | Kovacs et al. |
| 2019/0159907 A1 | 5/2019 | Roche et al. |
| 2019/0192305 A1 * | 6/2019 | Frankie .................... A61F 2/40 |
| 2019/0240035 A1 | 8/2019 | Lappin |
| 2019/0298537 A1 | 10/2019 | Gargac et al. |

\* cited by examiner

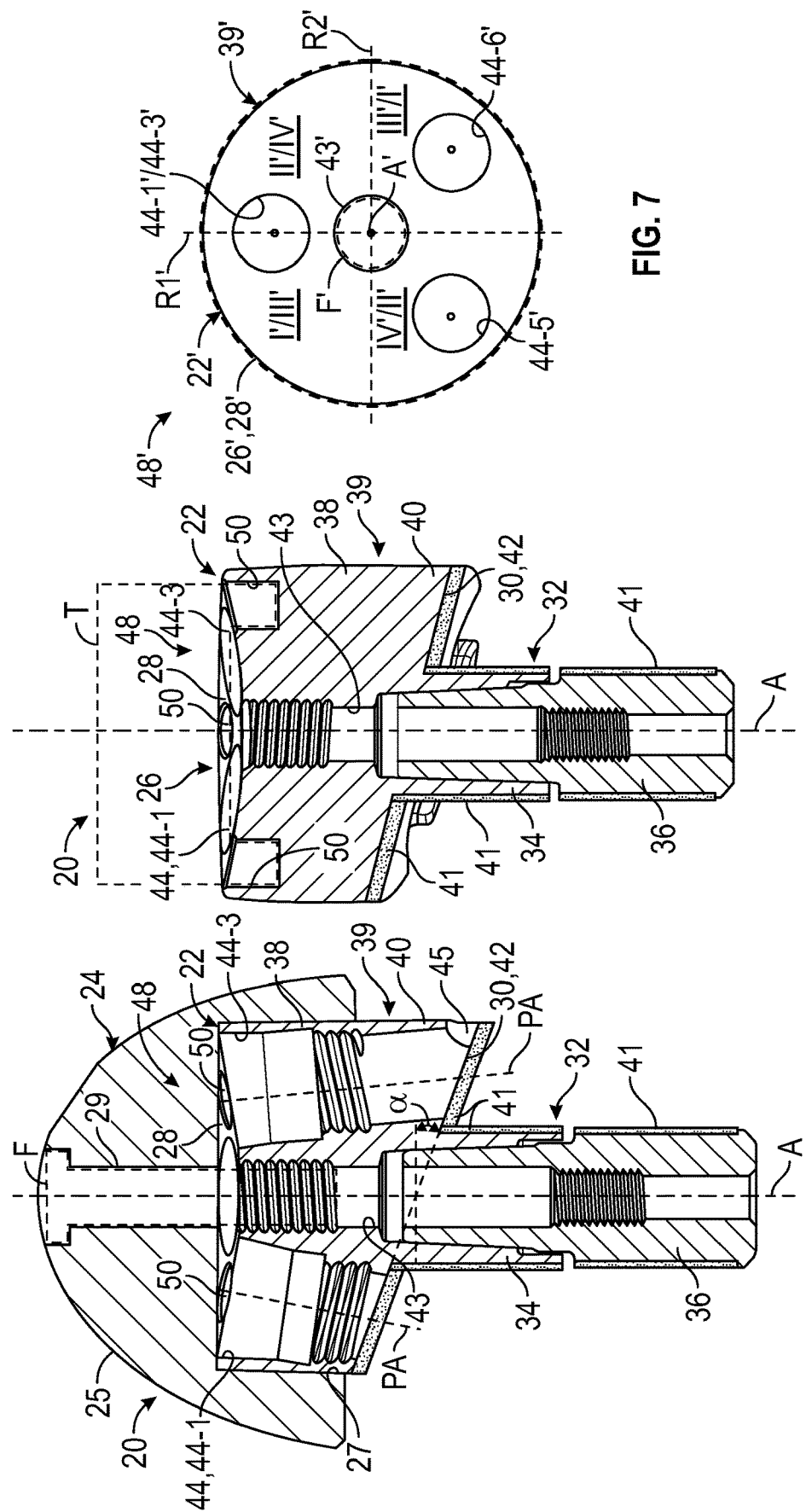

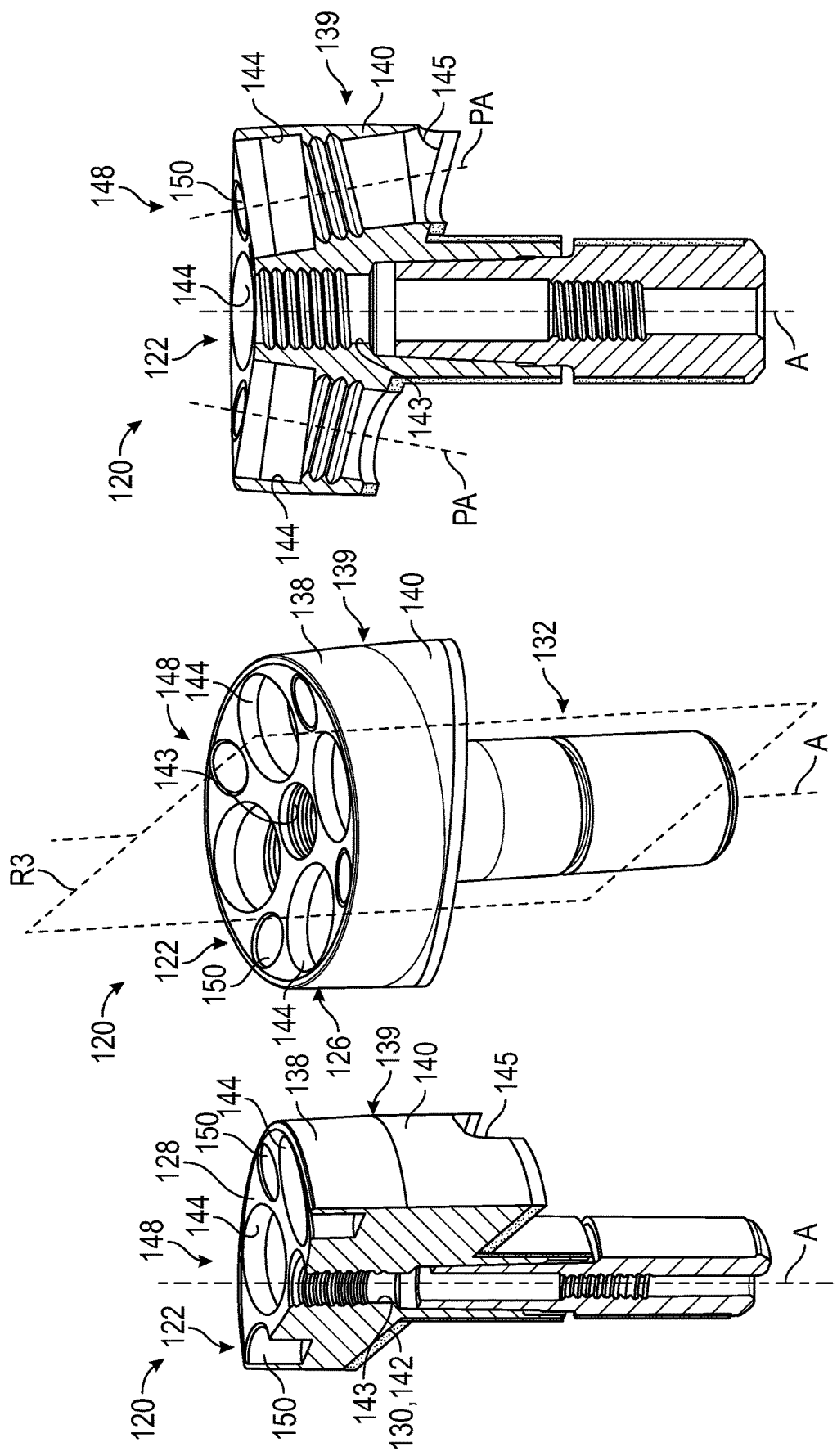

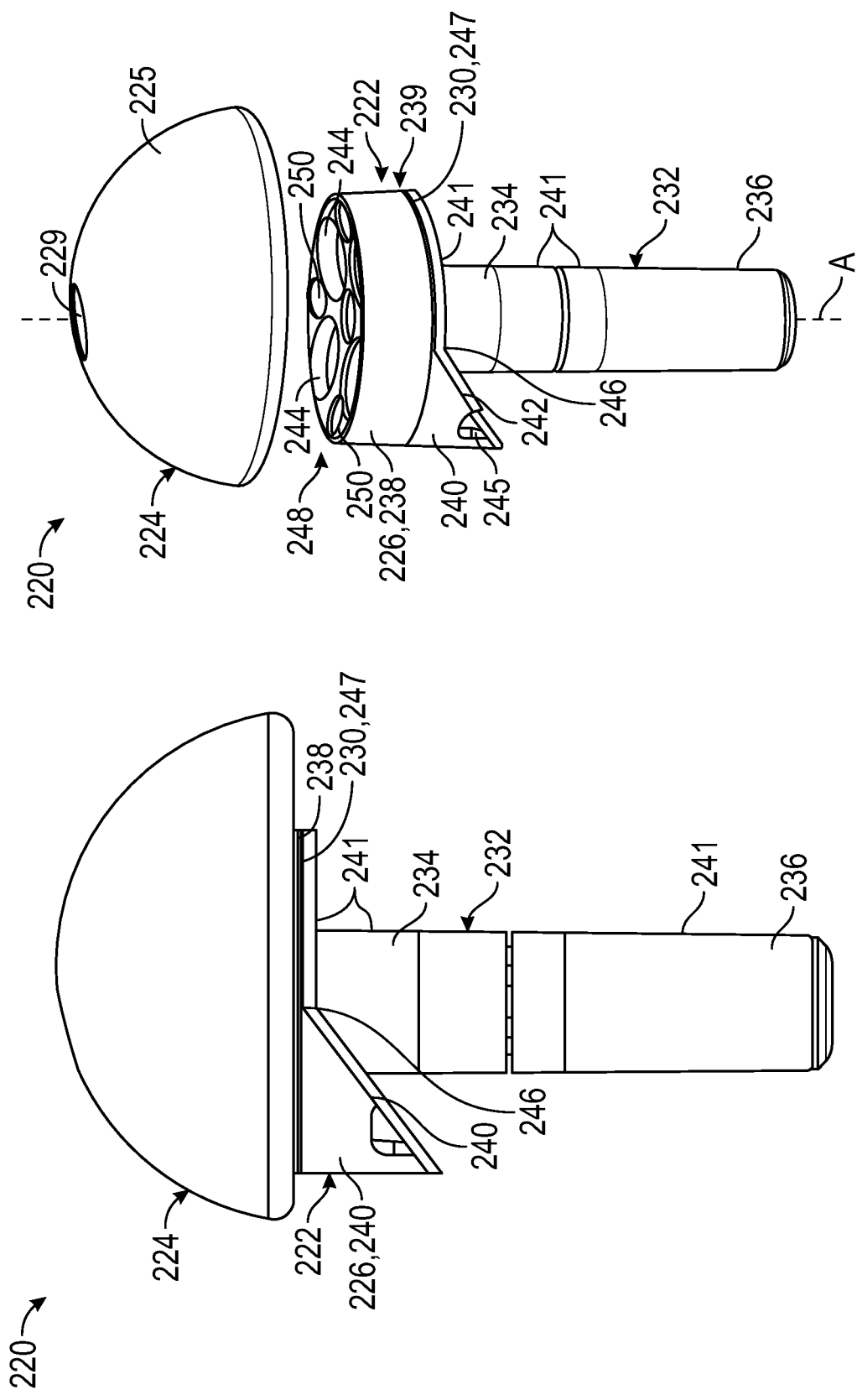

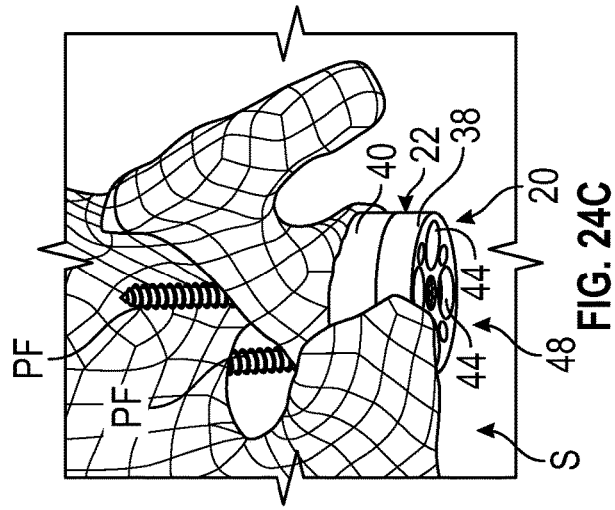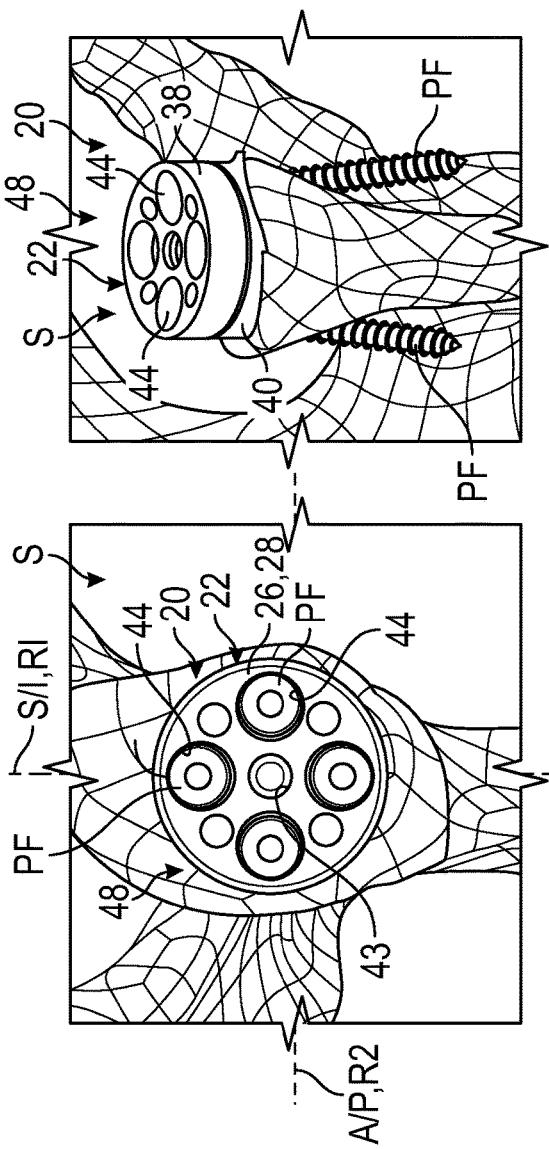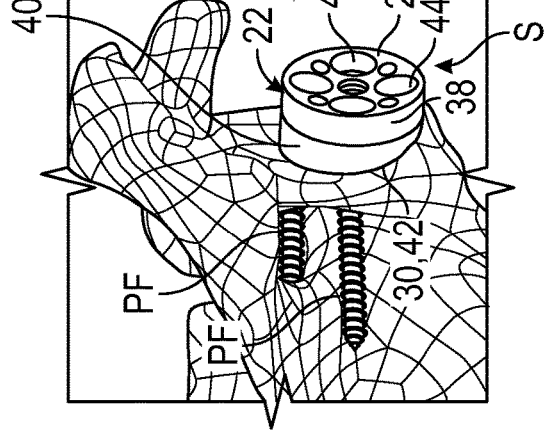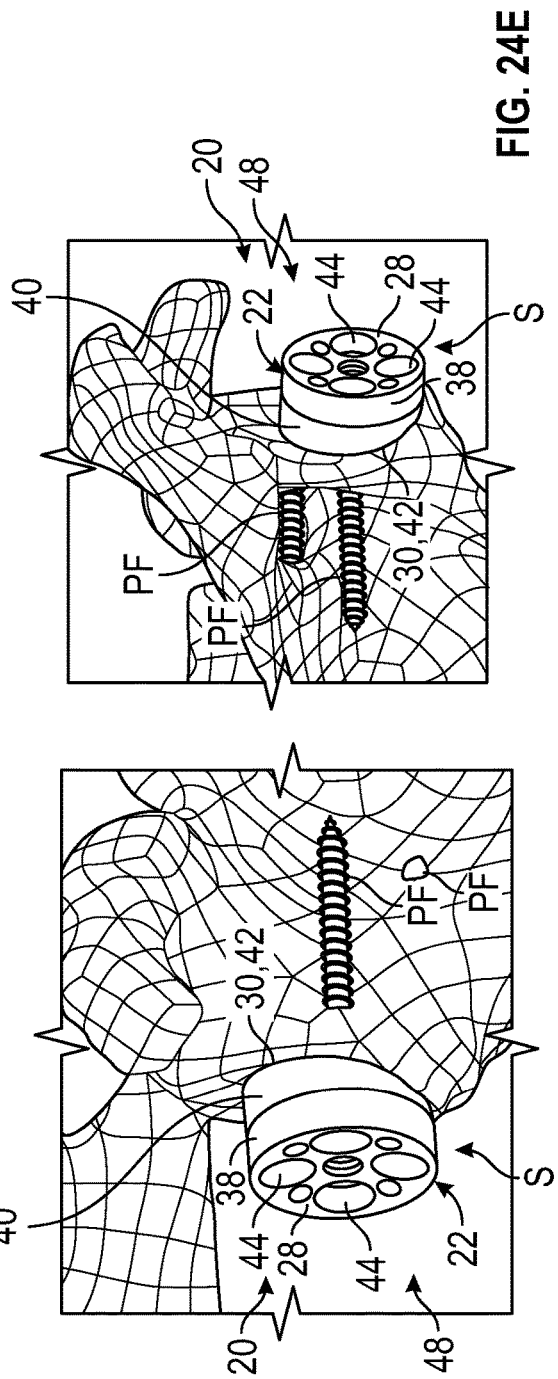
FIG. 24A  FIG. 24B  FIG. 24C  FIG. 24D  FIG. 24E

ORTHOPAEDIC IMPLANTS INCLUDING PERIPHERAL APERTURE ARRANGEMENTS

BACKGROUND

This disclosure relates to orthopaedic procedures and, more particularly, to orthopaedic implants and methods for repairing bone defects and restoring functionality to a joint.

Many bones of the human musculoskeletal system include articular surfaces. The articular surfaces articulate relative to other bones to facilitate different types and degrees of joint movement. The articular surfaces can erode or experience bone loss over time due to repeated use or wear or can fracture as a result of a traumatic impact. These types of bone defects can cause joint instability and pain.

Bone deficiencies may occur along the articular surfaces of the glenoid bone. Some techniques utilize a bone graft and/or implant to fill a defect in the glenoid bone. The implant may be secured to the glenoid utilizing one or more fasteners.

SUMMARY

This disclosure relates to orthopaedic implants and methods. The implants may be used during methods for repairing bone defects. The implants described herein may be utilized to restore functionality to a joint and include peripheral apertures arranged in one or more patterns for receiving fasteners to secure the implants at a surgical site.

An orthopaedic implant may include a baseplate including a plate body extending along a longitudinal axis between a front face and a rear face and may include an anchoring stem extending outwardly from the rear face. The plate body may include a main body portion establishing the front face, an augment portion extending outwardly from the main body portion to establish an augment face section of the rear face, and a plurality of peripheral apertures circumferentially distributed about the longitudinal axis. A perimeter of the plate body may be substantially circular. The peripheral apertures may be dimensioned to receive respective fasteners for securing the baseplate to a surgical site. The augment face section may be arranged transversely relative to the longitudinal axis, and first and second reference planes arranged perpendicular to each other extend along the longitudinal axis such that the first reference plane may bisect the augment face section. All peripheral apertures of the baseplate that are arranged about the longitudinal axis may be circumferentially offset from both of the first and second reference planes.

A kit for arthroplasty may include a set of baseplates and a plurality of fasteners. Each baseplate of the set of baseplates may include a plate body having a main body portion and a substantially wedge-shaped augment portion that cooperate to establish a front face and a rear face of the plate body, and a plurality of peripheral apertures extending between the front and rear faces. The peripheral apertures may be dimensioned to receive respective ones of the fasteners to secure the plate body to a surgical site. A first reference plane may extend along a longitudinal axis of the plate body to bisect the augment portion. The set of baseplates may include a first baseplate and a second baseplate, the peripheral apertures of the first baseplate may be circumferentially distributed about the longitudinal axis to establish a first pattern such that one or more of the peripheral apertures extend along the first reference plane, and the peripheral apertures of the second baseplate may be circumferentially distributed about the longitudinal axis to establish a second pattern, the second pattern may be circumferentially offset from the first pattern relative to the longitudinal axis, and the first and second patterns may have a common circumferential spacing between the respective peripheral apertures.

A method of installing an orthopaedic implant at a surgical site may include selecting a baseplate from a set of baseplates based on a surface profile of a surgical site. Each baseplate of the set of baseplates may include a plate body having a main body portion and a substantially wedge-shaped augment portion that cooperate to establish a front face and a rear face of the plate body, and a plurality of peripheral apertures may extend between the front and rear faces. A first reference plane may extend along the longitudinal axis to bisect the augment portion. The set of baseplates may include a first baseplate and a second baseplate, the peripheral apertures of the first baseplate may be arranged to establish a first pattern such that one or more of the peripheral apertures extend along the first reference plane, and the peripheral apertures of the second baseplate may be arranged to establish a second pattern circumferentially offset from the first pattern relative to the longitudinal axis, and the first and second patterns may have a common circumferential spacing between the respective peripheral apertures. The method may include positioning the selected baseplate relative to the surface profile of the surgical site and may include positioning a fastener in a respective one of the peripheral apertures to secure the selected baseplate to the surgical site.

BRIEF DESCRIPTION OF THE DRAWINGS

FIG. 5 illustrates a sectional view of the implant of FIG. 1.

FIG. 6 illustrates a sectional view of the baseplate of FIG. 2.

FIG. 7 illustrates an exemplary pattern or layout of peripheral apertures.

FIG. 11 illustrates a perspective, sectional view of the baseplate of FIG. 10.

FIG. 12 illustrates a perspective view of the baseplate of FIG. 8.

FIG. 13 illustrates a sectional view of the baseplate of FIG. 12.

FIG. 16 illustrates a side view of an exemplary orthopaedic implant including a baseplate and glenosphere.

FIG. 17 illustrates a perspective view of the implant of FIG. 14 with the glenosphere in an uninstalled position.

FIGS. 24A-24E illustrate the baseplate of FIG. 2 situated relative to a surgical site at different view angles.

DETAILED DESCRIPTION

Figure 2:
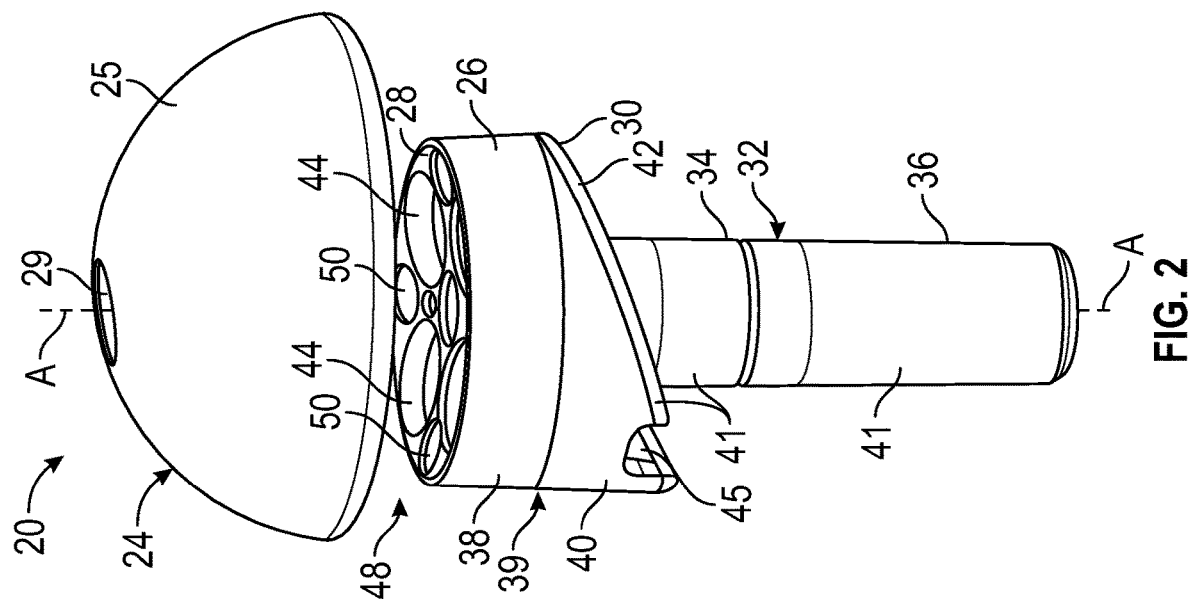
FIG. 2 illustrates a perspective view of the implant of FIG. 1 with the glenosphere in an uninstalled position.

This disclosure relates to orthopaedic implants and methods for repairing bone defects. The implants described herein may be utilized during arthroplasty procedures and incorporated into a shoulder prosthesis for restoring functionality to shoulders having advanced cartilage disease. The disclosed implants may be utilized to address complex glenoid pathology, which may have bony deficiencies at many different orientations relative to the Superior/Inferior (S/I) plane of the glenoid face. The implants can include augment geometries configured to fill bone voids along the glenoid face. The disclosed implants may include peripheral apertures arranged in patterns. The disclosed patterns can be utilized to improve fixation of the respective implant at the surgical site, which can lead to improved healing.

An orthopaedic implant according to an exemplary aspect of the present disclosure may include a baseplate including a plate body extending along a longitudinal axis between a front face and a rear face and may include an anchoring stem extending outwardly from the rear face. The plate body may include a main body portion establishing the front face and may include an augment portion extending outwardly from the main body portion to establish an augment face section of the rear face. A plurality of peripheral apertures may be circumferentially distributed about the longitudinal axis. The peripheral apertures may be dimensioned to receive respective fasteners for securing the baseplate to a surgical site. The augment face section may be arranged transversely relative to the longitudinal axis, and first and second reference planes may be arranged perpendicular to each other extend along the longitudinal axis such that the first reference plane bisects the augment face section, and all peripheral apertures of the baseplate that are arranged about the longitudinal axis may be circumferentially offset from both of the first and second reference planes.

In some embodiments, a perimeter of the plate body may be substantially circular.

In some embodiments, the anchoring stem may extend along the longitudinal axis.

In some embodiments, the plurality of peripheral apertures may be substantially equally distributed about the longitudinal axis.

In some embodiments, the plurality of peripheral apertures may include a total of four peripheral apertures.

In some embodiments, a third reference plane may extend along the longitudinal axis such that the first and third reference planes establish an acute angle, and a pair of the peripheral apertures may be circumferentially arranged along the third reference plane.

In some embodiments, the acute angle may be greater than 0 degrees but is less than 45 degrees.

In some embodiments, the acute angle may be between 30 degrees and 60 degrees.

In some embodiments, the plurality of peripheral apertures may include a total of four peripheral apertures.

In some embodiments, the four peripheral apertures may be substantially uniformly distributed about the longitudinal axis.

In some embodiments, the rear face may include a second face section arranged substantially perpendicular to the longitudinal axis, and the augment face section and the second face section may be joined at an interface to establish an obtuse angle.

In some embodiments, the obtuse angle may be between 140 degrees and 170 degrees.

In some embodiments, the implant includes a glenosphere including an articulating surface which may have a generally convex geometry, and the glenosphere may be secured to the baseplate adjacent the front face.

In some embodiments, the glenosphere may include a recess dimensioned to at least partially receive the main body portion of the baseplate.

In some embodiments, a perimeter of the main body portion of the baseplate may be dimensioned to cooperate with a perimeter of the recess to establish a Morse taper connection.

A kit for arthroplasty according to an exemplary aspect of the present disclosure may include a set of baseplates and a plurality of fasteners. Each baseplate of the set of baseplates may include a plate body having a main body portion and a substantially wedge-shaped augment portion that may cooperate to establish a front face and a rear face of the plate body, and may include a plurality of peripheral apertures extending between the front and rear faces. The peripheral apertures may be dimensioned to receive respective ones of the fasteners to secure the plate body to a surgical site. A first reference plane may extend along a longitudinal axis of the plate body to bisect the augment portion. The set of baseplates may include a first baseplate and a second baseplate. The peripheral apertures of the first baseplate may be circumferentially distributed about the longitudinal axis to establish a first pattern such that one or more of the peripheral apertures may extend along the first reference plane. The peripheral apertures of the second baseplate may be circumferentially distributed about the longitudinal axis to establish a second pattern, the second pattern may be circumferentially offset from the first pattern relative to the longitudinal axis, and the first and second patterns may have a common circumferential spacing between the respective peripheral apertures.

In some embodiments, the implant may include an anchoring stem which may extend outwardly from the rear face along the longitudinal axis. The implant may include glenosphere including an articulating surface which may have a generally convex geometry, and the glenosphere may be releasably secured to a respective one of the baseplates adjacent the front face.

In some embodiments, a perimeter of the main body portion may be substantially circular, and the peripheral apertures of both the first pattern and the second pattern may be substantially equally distributed about the longitudinal axis.

In some embodiments, a second reference plane may extend along the longitudinal axis and may be perpendicular to the first reference plane, and the second pattern may be established such that all peripheral apertures of the second baseplate that are arranged about the longitudinal axis may be circumferentially offset from both of the first and second reference planes.

A method of installing an orthopaedic implant at a surgical site according to an exemplary aspect of the present disclosure may include selecting a baseplate from a set of baseplates based on a surface profile of a surgical site. Each baseplate of the set of baseplates may include a plate body having a main body portion and a substantially wedge-shaped augment portion that may cooperate to establish a front face and a rear face of the plate body, and may include a plurality of peripheral apertures extending between the front and rear faces. A first reference plane may extend along the longitudinal axis to bisect the augment portion. The set of baseplates may include a first baseplate and a second baseplate. The peripheral apertures of the first baseplate may be arranged to establish a first pattern such that one or more of the peripheral apertures may extend along the first reference plane. The peripheral apertures of the second baseplate may be arranged to establish a second pattern circumferentially offset from the first pattern relative to the longitudinal axis, and the first and second patterns may have a common circumferential spacing between the respective peripheral apertures. The method may include positioning the selected baseplate relative to the surface profile of the surgical site and may include positioning a fastener in a respective one of the peripheral apertures to secure the selected baseplate to the surgical site.

In some embodiments, the plurality of peripheral apertures may include a total of four peripheral apertures, a second reference plane may extend along the longitudinal axis and may be perpendicular to the first reference plane, two of the peripheral apertures of the first pattern may be arranged along the first reference plane, and another two of the peripheral apertures of the first pattern may be arranged along the second reference plane, and the second pattern may be established such that all peripheral apertures of the second baseplate may be circumferentially offset from both the first and second reference planes.

In some embodiments, an anchoring stem may extend outwardly from the rear face along the longitudinal axis. The method may include positioning the anchoring stem in a bone hole along the surgical site and may include securing a glenosphere to the selected baseplate. The glenosphere may include an articulating surface having a generally convex geometry.

FIGS. 1-6 illustrate an exemplary orthopedic implant 20. The implant 20 can be utilized for various surgical procedures, such as arthroplasty procedures to repair a joint. For example, the implant 20 can be incorporated into a shoulder prosthesis. Although the implants disclosed herein primarily refer to repair of a defect in a glenoid during a shoulder reconstruction, such as a reverse shoulder procedure, it should be understood that the disclosed implants may be utilized in other locations of the patient and other surgical procedures.

Figure 1:
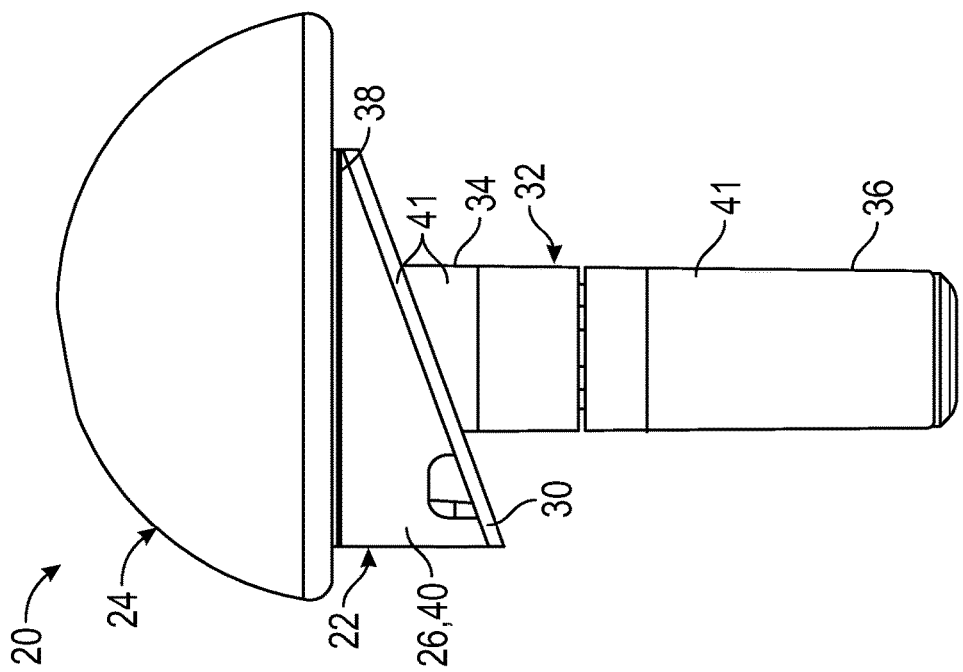
FIG. 1 illustrates a side view of an exemplary orthopaedic implant including a baseplate and glenosphere.

Referring to FIGS. 1-2, the implant 20 includes a baseplate 22 and a glenosphere 24 releasably secured to the baseplate 22. The baseplate 22 includes a plate body 26 extending along a longitudinal axis A (FIG. 2) between a front (or first) face 28 (FIG. 2) and a rear (or second) face 30 generally opposed to the front face 28. The rear face 30 may generally correspond to a medial side of a patient, and the front face 28 may generally correspond to a lateral side of the patient when implanted in a surgical site, for example.

The baseplate 22 can include a post or anchoring stem 32 extending outwardly from the rear face 30. A central axis of the anchoring stem 32 may be offset from the longitudinal axis A. In FIG. 2, the anchoring stem 32 extends along the longitudinal axis A and has a substantially cylindrically geometry. The anchoring stem 32 may be dimensioned for insertion in a glenoid or bone hole which may be formed to secure the baseplate 22, for example.

The anchoring stem 32 can include a first stem portion 34 and a second stem portion 36. The first stem portion 34 can be integrally formed with the plate body 26. The anchoring stem 32 and plate body 26 may be separate and distinct components. The first stem portion 34 can be mechanically attached or otherwise secured to the second stem portion 36 utilizing various techniques, such as threading, bonding and welding. In FIGS. 5-6, the first stem portion 34 and second stem portion 36 are connected via a reversed taper connection. The anchoring stem 32 may be a single component.

Figure 4:
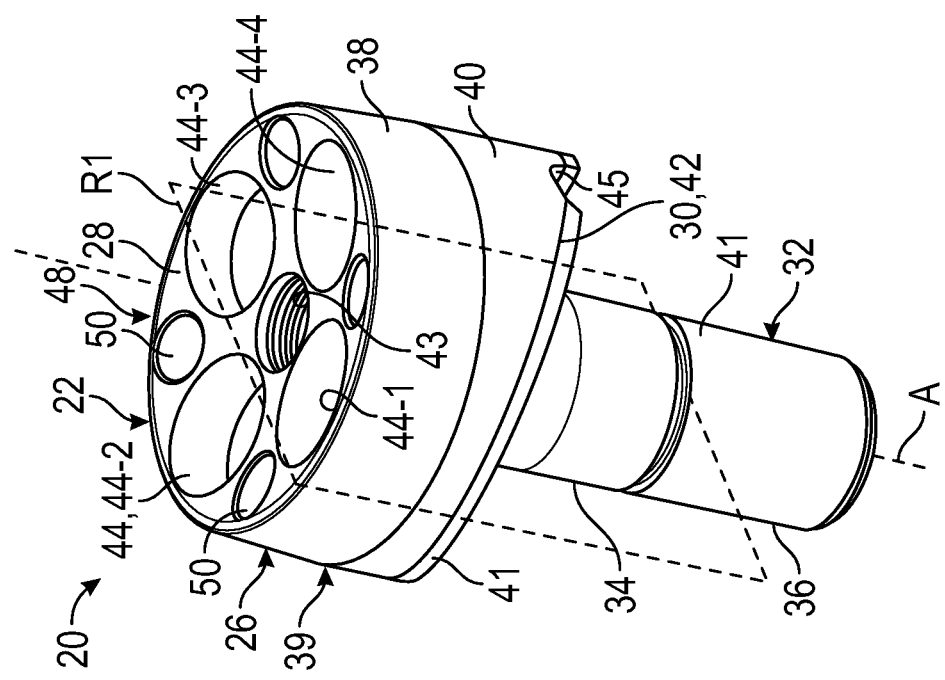
FIG. 4 illustrates a perspective view of the baseplate of FIG. 2.
Figure 3:
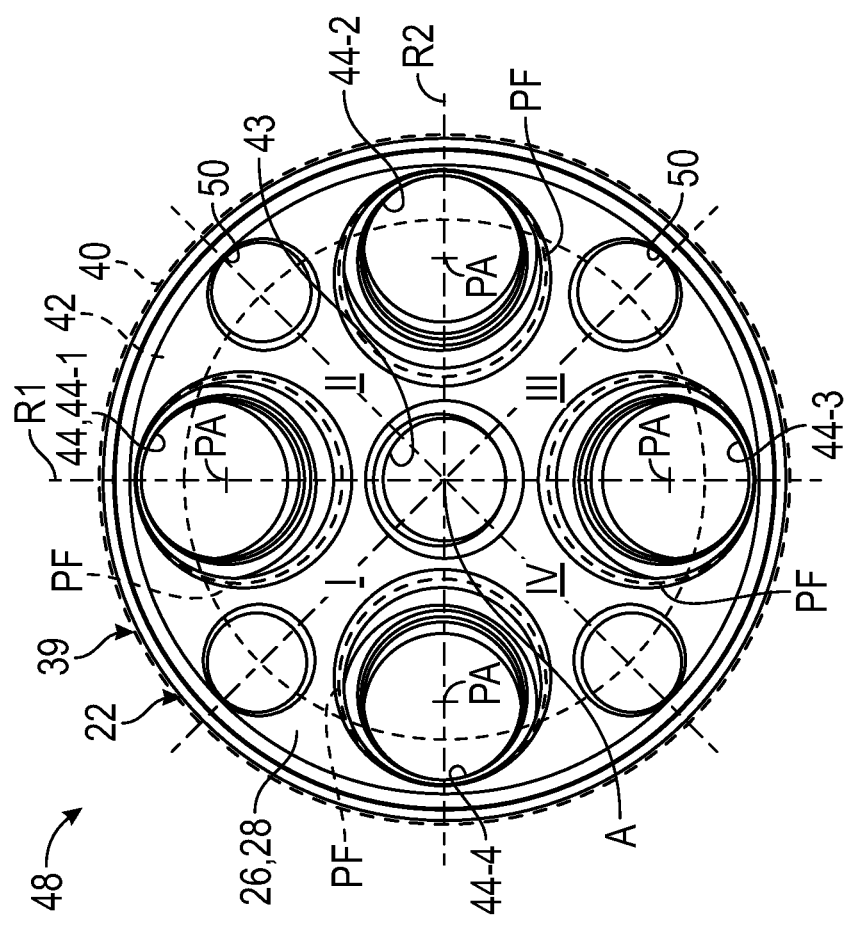
FIG. 3 illustrates a plan view of the baseplate of FIG. 2 including an exemplary pattern or layout of peripheral apertures.

Referring to FIG. 2, with continuing reference to FIG. 1, the plate body 26 includes a main body portion 38 and an augment portion 40 extending outwardly from the main body portion 38. The main body portion 38 may establish a perimeter 39 of the plate body 26. The perimeter 39 of the plate body 26 can have an elliptical geometry, for example. In FIGS. 3-4, the perimeter 39 of the plate body 26 has a substantially circular geometry. A substantially circular geometry may reduce a reaming width and complexity of preparing a surgical site to accept the implant 20. The main body portion 38 establishes a front face 28 of the plate body 26. The augment portion 40 establishes at least a portion of the rear face 30.

Various materials can be utilized to form the baseplate 22 and glenosphere 24. The baseplate 22 and glenosphere 24 may be made of metallic materials. The implant 20 can include one or more coatings or layers 41 deposited along surfaces of the baseplate 22. Example coatings 41 can include calcium phosphate (CaP) having a porous construction for promoting bone growth.

The augment portion 40 can be dimensioned to approximate various defect geometries and surface contours that may be encountered along a surgical site. The augment portion 40 may be configured to at least partially fill a bone void in a glenoid. The augment portion 40 can be dimensioned to establish a relative lesser or greater overall volume of the baseplate 22. For example, a cross section of the augment portion 40 can have a substantially wedge-shaped geometry and may extend across a full width of the main body portion 38 (e.g., "full-wedge"), as illustrated by FIGS. 1 and 5-6. The augment portion 40 can have other shaped or profiles, such as a generally step-shaped geometry.

The augment portion 40 extends outwardly from the main body portion 38 to establish an augment face section 42 of the rear face 30. The augment face section 42 can be substantially planar. The augment face section 42 can be generally concave or convex. The augment face section 42 can substantially slope or extend across the full width of the main body portion 38, with the augment face section 42 arranged transversely relative to the longitudinal axis A, as illustrated in FIGS. 2 and 4. The augment portion 40 can be dimensioned such that innermost (e.g., lowest) and outermost (e.g., highest) points of the augment face section 42 relative to the longitudinal axis A are defined along a perimeter of the augment portion 40.

The augment face section 42 can be arranged at various angles relative to the main body portion 38 to establish a relative lesser or greater overall volume of the baseplate 22. The augment face section 42 may establish an acute angle α relative to a reference plane that is perpendicular to the longitudinal axis A, as illustrated by FIG. 5. The angle α may be greater than 0 degrees but may be less than 45 degrees. The angle α can be equal to or greater than approximately 5 degrees and less than or equal to approximately 45 degrees, for example. The angle α may be approximately 10 or 20 degrees. For the purposes of this disclosure, the term "approximately" means ±5 percent of the stated value unless otherwise disclosed.

The baseplate 22 may include a plurality of peripheral apertures (or holes) 44 along the front face 28 of the plate body 26. The peripheral apertures 44 may extend between the front face 28 and rear face 30 of the plate body 26, with at least some or each of the peripheral apertures 44 extending through a thickness of the augment portion 40 between the front face 28 and the augment face section 42 of the rear face 30, as illustrated in FIG. 5. Each peripheral aperture 44 can be dimensioned to receive a respective peripheral fastener PF (shown in dashed lines in FIG. 3 for illustrative purposes) for securing the baseplate 22 to a surgical site. Example fasteners may include compression screws, as illustrated by the peripheral fasteners PF of FIGS. 24A-25E.

The baseplate 22 can include one or more recesses 50 extending inwardly from the front face 28 of the plate body 26. The recesses 50 can be dimensioned to receive an inserter or tooling T to insert or otherwise position the baseplate 22 along a surgical site (shown in dashed lines in FIG. 6 for illustrative purposes). The recesses 50 may be omitted.

The glenosphere 24 includes an articulating surface 25 which may have a generally convex geometry, as illustrated by FIGS. 2 and 5. The articulating surface 25 may cooperate with a humeral component having a generally concave, complementary geometry. The front face 28 can have a generally concave geometry, as illustrated in FIGS. 5-6. The glenosphere 24 may be omitted and the front face 28 may serve as an articulating surface that cooperates with a humeral component having a generally convex, complementary geometry.

The glenosphere 24 can be mechanically attached or releasably secured to the baseplate 22 adjacent to the front face 28, as illustrated by FIGS. 1 and 5. In FIG. 5, the glenosphere 24 may include a recess 27 dimensioned to at least partially receive the main body portion 38 of the baseplate 22 adjacent to the front face 28. The recess 27 may be dimensioned to encircle a rim of the baseplate 22 along the front face 28. A perimeter of the main body portion 38 of the baseplate 22 can be dimensioned to cooperate with a perimeter of the recess 27 to establish a Morse taper connection to secure the glenosphere 24 to the baseplate 22. The plate body 26 can include a central aperture 43 extending along the longitudinal axis A. The glenosphere 24 can include an aperture 29 dimensioned to receive a fastener F (shown in dashed lines in FIG. 5 for illustrative purposes). The fastener F can include threading that cooperates with threading along the central aperture 43. The fastener F can serve to align the glenosphere 24 relative to the longitudinal axis A and/or secure the glenosphere 24 to the baseplate 24. The fastener F and/or apertures 29, 43 and may be omitted. The anchoring stem 32 may be omitted and the aperture 43 may be dimensioned to receive a fastener such as a compression screw for securing the baseplate 24 to a surgical site (illustrated by fastener F' of FIG. 7 in dashed lines in for illustrative purposes).

Referring to FIG. 3, with continuing reference to FIGS. 1-2, the peripheral apertures 44 can be circumferentially distributed about the longitudinal axis A to establish a respective pattern (or layout) 48. Each pattern 48 can be predefined with respect to a geometry of the baseplate 22 and augment portion 40. A perimeter of the augment portion 40 is shown in dashed lines for illustrative purposes. The pattern 48 can be defined with respect to the front face 28 of the plate body 26. The peripheral apertures 44 may be arranged relative to first and second reference planes R1, R2 to establish the pattern 48. The first and second reference planes R1, R2 may be arranged perpendicular to each other and can extend along the longitudinal axis A such that the first reference plane R1 may bisect the augment face section 42 of the augment portion 40. The augment portion 40 can be dimensioned such that the innermost (e.g., lowest) and outermost (e.g., highest) points of the augment face section 42 relative to the longitudinal axis A are defined along the first reference plane R1.

FIG. 4 illustrates a perspective view of the baseplate 22 relative to the reference plane R1. FIG. 5 illustrates a sectional view of the baseplate 22 taken along the first reference plane R1 and through a maximum thickness of the augment portion 40. FIG. 6 illustrates a sectional view of the baseplate 22 taken along the second reference plane R2. The first and second reference planes R1, R2 may divide the baseplate 22 into four quadrants I-VI. The baseplate 22 may be symmetrical on opposed sides of the first reference plane R1. The baseplate 22 may be asymmetrical on opposed sides of the first reference plane R1.

The pattern 48 may be defined such that one or more of the peripheral apertures 44 extend along the first reference plane R1. In FIG. 3, the pattern 48 may be established by a total of four peripheral apertures 44. The four peripheral apertures 44 can be spaced at approximately 90 degree increments about the longitudinal axis A such that the apertures 44 are substantially equally distributed about the longitudinal axis A. Two of the peripheral apertures 44 may extend along and be aligned with the first reference plane R1 (indicated at 44-1, 44-3), and another two of the peripheral apertures 44 may extend along and be aligned with the second reference plane R2 (indicated at 44-2, 44-4). The pattern 48 may be defined such that the baseplate 22 is free of any peripheral apertures between adjacent pairs of the peripheral apertures 44.

Other example patterns can be utilized with any of the baseplates disclosed herein, and fewer or more than four peripheral apertures can be utilized. One or more of the peripheral apertures 44-1 to 44-4 can be omitted. For example, apertures 44-2, 44-4 can be omitted such that the pattern 48 is established by the pair of opposed apertures 44-1, 44-3, or vice versa. In FIG. 7, pattern 48' includes a total of three peripheral apertures 44' (indicated at 44-1'/44-3', 44-5' and 44-6'). Aperture 44-1'/44-3' may extend along the first reference plane R1'. Apertures 44-5', 44'6 may be circumferentially offset or otherwise spaced apart from both the first reference plane R1' and second reference plane R2'.

Referring to FIG. 5, with continuing reference to FIGS. 2-4, each peripheral aperture 44 may extend along a respective passage axis PA. The passage axis PA can be parallel to the longitudinal axis A. In FIG. 5, the passage axis PA is substantially transverse to the longitudinal axis A, which can increase a spacing between terminal ends of adjacent fasteners inserted through the peripheral apertures 44. At least some of the peripheral apertures 44 can intersect a respective notch 45 along the perimeter 39 of the plate body 26.

Various patterns or layouts of peripheral apertures can be established to approximate a variety of different surface profiles and void geometries that may be encountered by the surgeon in preparation of surgery. The surgeon can be provided with a set of orthopedic implants in a kit for arthroplasty, including any of the implants and patterns disclosed herein. The kit can include a set of baseplates having any of the baseplates, augment geometries and patterns of the peripheral apertures disclosed herein. The kit can also include fasteners that are received in respective peripheral apertures to secure the respective baseplate to the surgical site.

Figure 8:
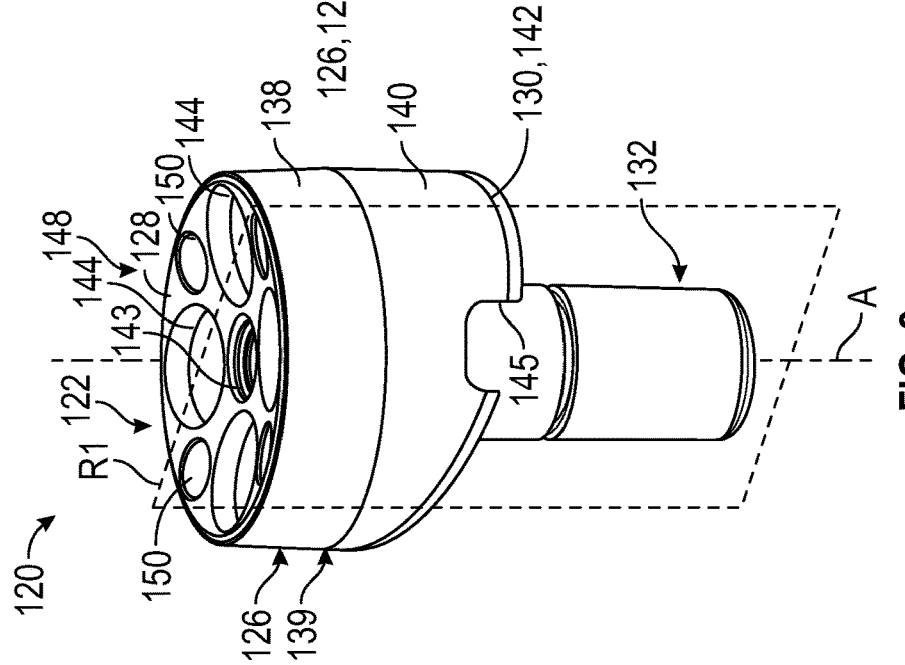
FIG. 8 illustrates a perspective view of a baseplate.

FIGS. 8-13 illustrate an exemplary orthopedic implant 120. Referring to FIG. 8, the implant 120 may include a baseplate 122 having a plate body 126 extending along a longitudinal axis A between a front (or first) face 128 and a rear (or second) face 130 generally opposed to the front face 128. The baseplate 122 can include a central post or anchoring stem 132 which may extend outwardly from the rear face 130 along a longitudinal axis A. The plate body 126 may include a main body portion 138 and an augment portion 140 may extend outwardly from the main body portion 138. The main body portion 138 may establish a front face 128 of the plate body 126. The augment portion 140 may establish at least a portion of the rear face 130 and can have a substantially wedge-shaped geometry.

The baseplate 122 may include a plurality of peripheral apertures (or holes) 144 along the front face 128 of the plate body 126 for securing the baseplate 122 to a surgical site. The peripheral apertures 144 may extend between the front face 128 and rear face 130, with at least some or each of the peripheral apertures 144 extending through a thickness of the augment portion 140 between the front face 128 and an augment face section 142 of the rear face 130, as illustrated in FIG. 13. Each peripheral aperture 144 can be dimensioned to receive a respective fastener for securing the baseplate 122 to a surgical site.

Figure 9:
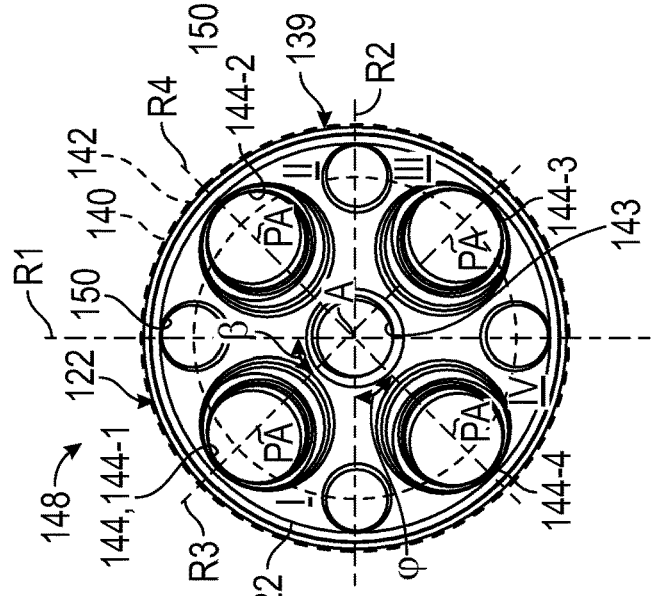
FIG. 9 illustrates a plan view of the baseplate of FIG. 8 including an exemplary pattern or layout of peripheral apertures.

Referring to FIG. 9, with continuing reference to FIG. 8, the peripheral apertures 144 can be circumferentially distributed about the longitudinal axis A to establish a respective pattern (or layout) 148. The peripheral apertures 144 may be arranged relative to first and second reference planes R1, R2 such that the pattern 148 differs from the pattern 48 of peripheral apertures 44 (FIG. 3). The first reference plane R1 may bisect an augment face section 142 of augment portion 140 (shown in dashed lines for illustrated purposes). At least some of the peripheral apertures 144 may be circumferentially offset (e.g., "obliquely" arranged) or are otherwise spaced apart from both of the first and second reference planes R1, R2 with respect to the longitudinal axis A. In FIG. 9, all peripheral apertures 144 of the baseplate 122 that are arranged about the longitudinal axis A may be circumferentially offset from both of the first and second reference planes R1, R2 with respect to the longitudinal axis A.

Various quantities of peripheral apertures 144 can be utilized to establish the pattern 148. In FIG. 9, the baseplate 122 may include a total of four peripheral apertures 144 (indicated at 144-1 to 144-4). However, it should be appreciated that fewer or more than four peripheral apertures 144 can be utilized in accordance with the teachings disclosed herein. The peripheral apertures 144 are substantially uniformly distributed about the longitudinal axis A. The peripheral apertures 144 may be non-uniformly distributed about the longitudinal axis A such that some adjacent pairs of apertures 144 are relatively closer or further away than other adjacent pairs of apertures 144.

The baseplates 22, 122 can be provided as a set of baseplates (e.g., first and second baseplates), with each baseplate 22, 122 establishing a respective pattern 48, 148 (e.g., first and second patterns). The peripheral apertures 44 of the pattern 48 and the peripheral apertures 144 of the pattern 148 can have a common number of peripheral apertures 44/144 and can have a common circumferential spacing between respective adjacent apertures 44/144 relative to the longitudinal axis A. The baseplate 122 can have the same external profile or shape as the baseplate 22.

Figure 10:
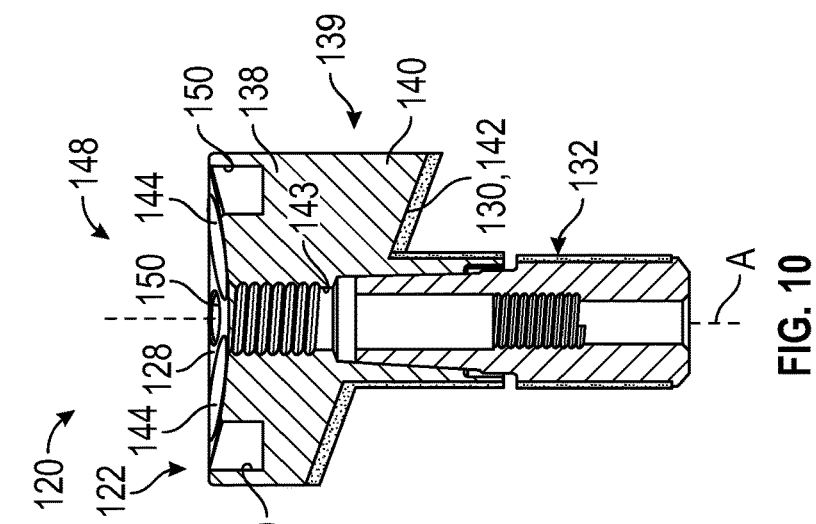
FIG. 10 illustrates a sectional view of the baseplate of FIG. 8.

The peripheral apertures 144 can be arranged such that the pattern 148 is circumferentially offset from the pattern 48 (FIG. 3) relative to the longitudinal axis A. For example, the baseplate 122 can be free of any peripheral apertures 144 along the first reference plane R1 as illustrated by FIGS. 9-11. FIGS. 10-11 illustrate a sectional view of the baseplate 122 taken along the first reference plane R1 and through a maximum thickness of the augment portion 140. The peripheral apertures 44, 144 of both patterns 48, 148 can be substantially equally distributed about the longitudinal axis A.

In FIG. 9, a third reference plane R3 may extend along the longitudinal axis A such that the first and third reference planes R1, R3 establish an acute angle β. A fourth reference plane R4 may extend along the longitudinal axis A such that the second and fourth reference planes R2, R4 establish an acute angle φ. The third reference plane R3 may be perpendicular to the fourth reference plane R4. One or more of the apertures 144 may be circumferentially arranged along the third reference plane R3, and one or more of the apertures 144 may be circumferentially arranged along the fourth reference plane R4. An opposed pair of the apertures 144-1, 144-3 may be arranged along the third reference plane R3 (see also FIGS. 12-13), and another opposed pair of the apertures 144-2, 144-4 may be arranged along the fourth reference plane R4, as illustrated in FIG. 9. The angle β and/or angle φ may be greater than 0 degrees, such as between approximately 25 degrees and approximately 75 degrees, or more narrowly between approximately 30 degrees and approximately 60 degrees such as approximately 45 degrees. The angle β and/or angle φ may be greater than 0 degrees but may be less than 45 degrees. The angle β and angle φ can be the same or can differ. The angle β and angle φ may be equal, and the pattern 148 of apertures 144 may be circumferentially offset or shifted from the pattern 48 of apertures 44 by the angle β relative to the longitudinal axis A.

Figure 14:
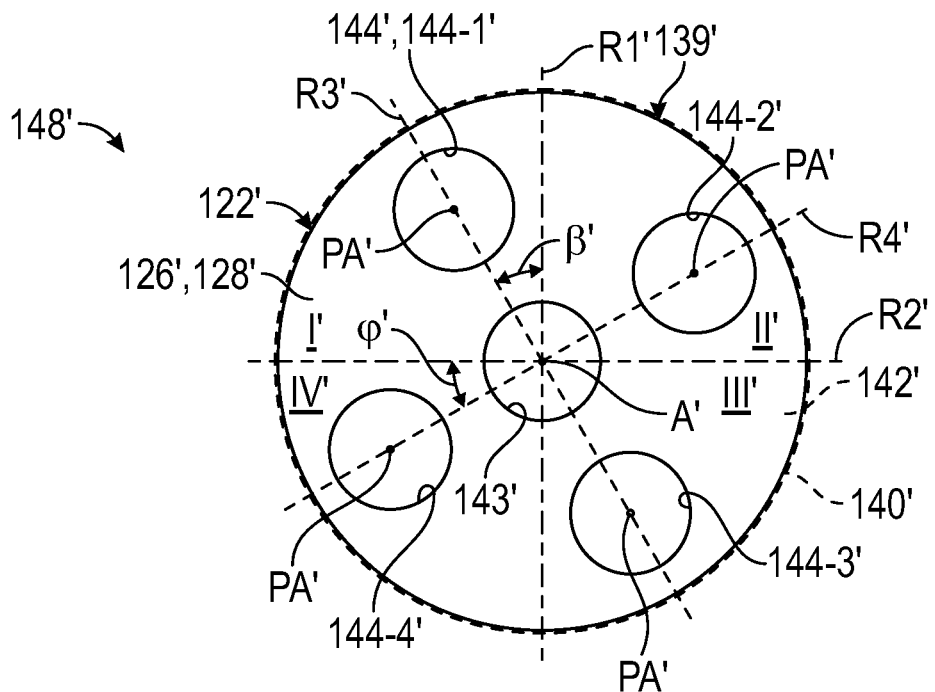
FIGS. 14-15 illustrate exemplary patterns or layouts of peripheral apertures.
Figure 15:
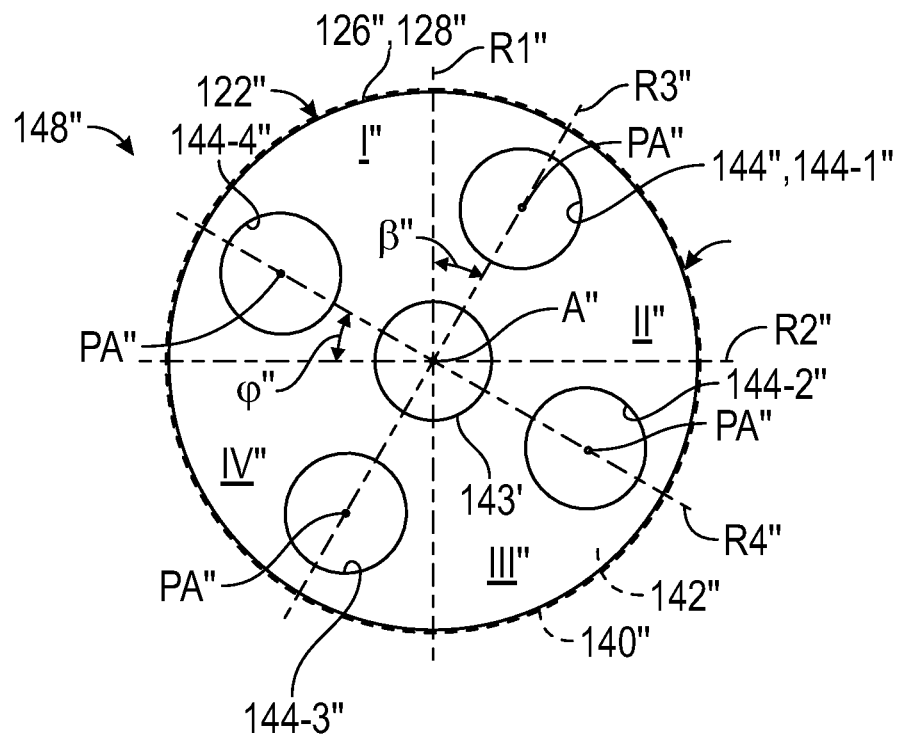

In the embodiment of FIG. 14, pattern 148' may circumferentially offset or shifted from pattern 48 (FIG. 3) in a counterclockwise direction relative to longitudinal axis A'. The apertures 144' of the pattern 148' can be circumferentially offset to a lesser amount than the apertures 144 of the pattern 148. Angle β' and angle φ' may be less than 45 degrees, such as about 30 degrees. In FIG. 15, pattern 148" may be circumferentially offset or shifted from pattern 48 in a clockwise direction relative to longitudinal axis A". Angle β" and angle φ" may be less than 45 degrees, such as about 30 degrees. The disclosed values of angle β and/or angle φ can be positive (e.g., clockwise) or negative (e.g., counterclockwise) relative to the respective reference planes R1, R2.

Fewer or more than four circumferentially offset peripheral apertures can be utilized. One or more of the peripheral apertures 144-1 to 144-4 can be omitted. For example, apertures 144-2, 144-4 can be omitted such that the pattern 148 may be established by the pair of opposed apertures 144-1, 144-3, or vice versa. As another example, apertures 144-1, 144-2 can be omitted such that the pattern 148 is established by apertures 144-3, 144-4, or vice versa.

FIGS. 16-19 illustrate an exemplary orthopedic implant 220. Referring to FIGS. 16-17, the implant 220 includes a baseplate 222 having a plate body 226 extending along a longitudinal axis A between a front (or first) face 228 and a rear (or second) face 230 which may generally opposed to the front face 228. The baseplate 222 can include a central post or anchoring stem 232 which may extend outwardly from the rear face 230 along a longitudinal axis A. The plate body 226 includes a main body portion 238 and an augment portion 240 which may extend outwardly from the main body portion 238. The main body portion 238 can establish a front face 228 of the plate body 226. The augment portion 240 can establish at least a portion of the rear face 230 and can have a substantially wedge-shaped geometry.

Figure 19:
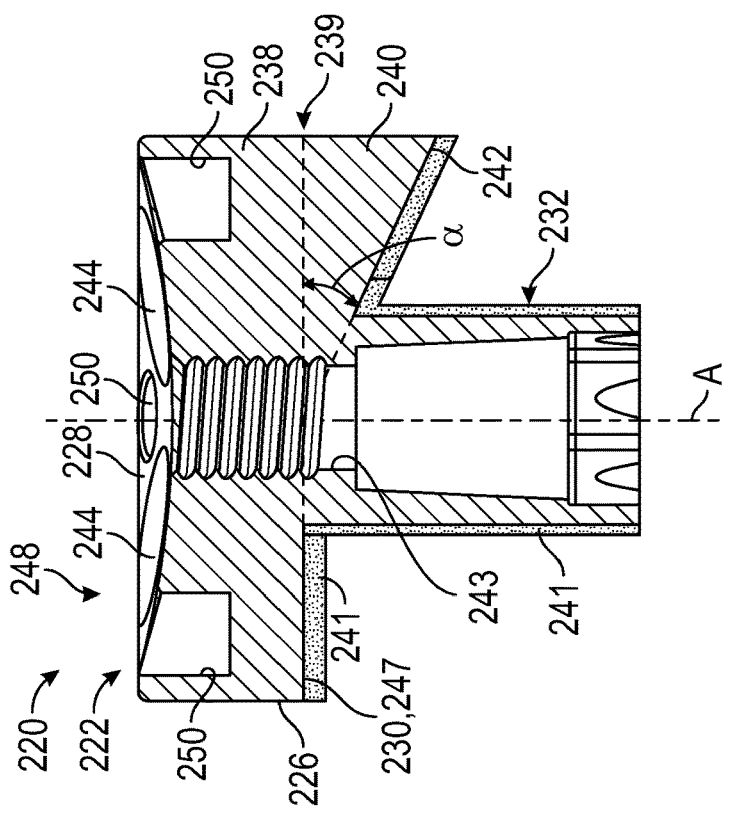
FIGS. 18-19 illustrate sectional views of the baseplate of FIG. 16.

The augment portion 240 may be dimensioned to extend less than a full width of the main body portion 238 (e.g., "partial-wedge"). The rear face 230 may include an augment face section 242 established by the augment portion 240 and a second face section 247 joined at an interface 246. The second face section 247 can be arranged along a reference plane that may be substantially perpendicular to the longitudinal axis A, as illustrated by FIG. 19. FIG. 19 illustrates a sectional view through a maximum thickness of the augment portion 240. The augment portion 240 can be dimensioned to span approximately ½ of a width of the plate body 226, with the interface 246 established along the longitudinal axis A (e.g., "half-wedge"), as illustrated by FIG. 16. The augment portion 240 can be dimensioned to extend less than or greater than ½ of the width of the plate body 226, such as approximately ¾ of the width of the plate body 226 (e.g., "¾ wedge").

The augment face section 142 may establish an acute angle $\alpha$ relative to a reference plane that may be perpendicular to the longitudinal axis A, as illustrated in FIG. 19. The angle $\alpha$ can be equal to or greater than approximately 5 degrees and more narrowly less than or equal to approximately 45 degrees, for example. The angle $\alpha$ may be approximately 15, 25 or 35 degrees. The geometry of the augment portion 240 can be utilized with any of the baseplates and/or patterns of peripheral apertures disclosed herein.

Figure 18:
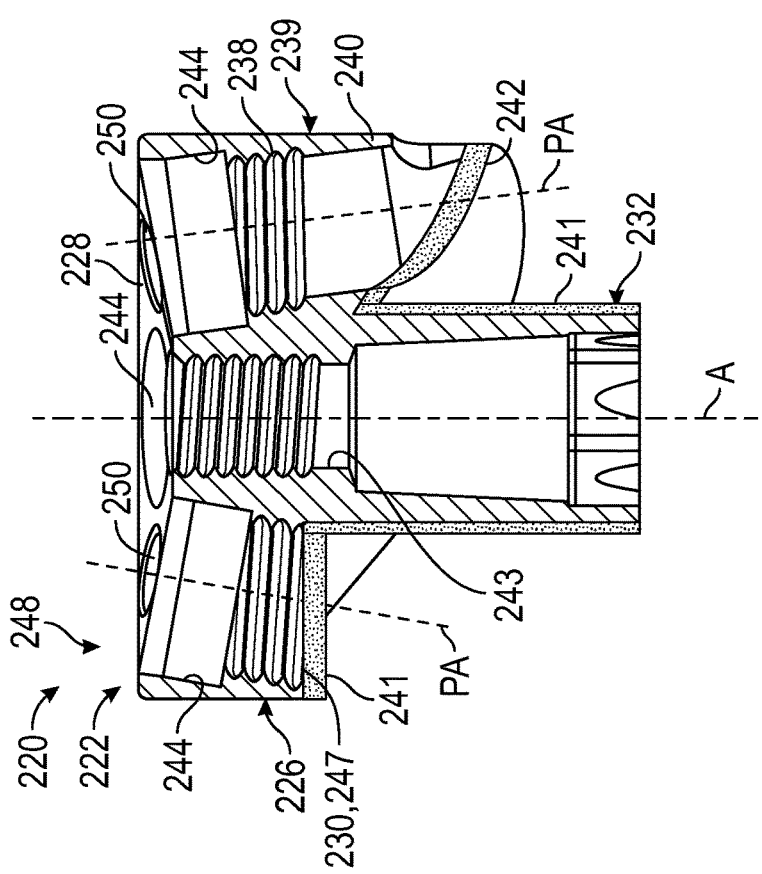

The baseplate 222 may include a plurality of peripheral apertures (or holes) 244 along the front face 228 of the plate body 226 for securing the baseplate 222 to a surgical site, as illustrated in FIG. 17. The peripheral apertures 244 can extend between the front face 228 and rear face 230 of the plate body 226, with at least some or each of the peripheral apertures 244 extending through a thickness of the augment portion 240 between the front face 228 and an augment face section 242 of the rear face 230, as illustrated in FIG. 18. In FIG. 18, only some of the peripheral apertures 244 may extend through the augment portion 240, and at least one of the apertures 244 may extend between the front face 288 and the second face section 247 of the rear face 230. Each peripheral aperture 244 may be dimensioned to receive a respective fastener for securing the baseplate 222 to a surgical site.

Referring to FIGS. 17-19, with continuing reference to FIG. 16, the peripheral apertures 244 can be circumferentially distributed about the longitudinal axis A to establish a respective pattern (or layout) 248. The pattern 248 can be arranged according to any of the patterns disclosed herein. The pattern 248 may correspond to the pattern 148 of FIG. 9, with FIG. 18 being a sectional view taken along the third or fourth reference planes R3, R4, and FIG. 19 being a sectional view of the baseplate 222 of taken along the first reference plane R1.

Figure 20:
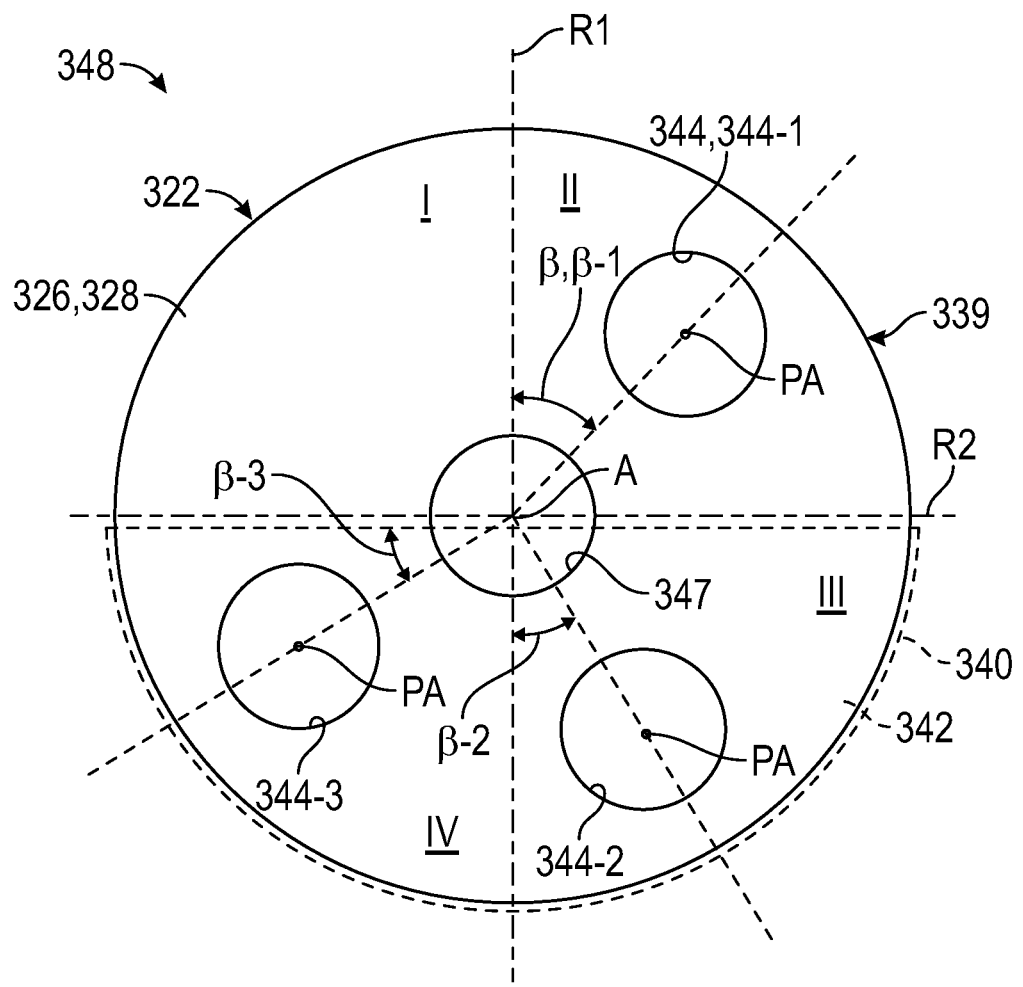
FIG. 20 illustrates an exemplary patterns or layouts of peripheral apertures.

FIG. 20 illustrates an exemplary pattern (or layout) 348. Baseplate 322 includes an augment portion 340 (shown in dashed lines) that may extend less than a full width of the plate body 326. Peripheral apertures 344 (indicated at 344-1 to 344-3) may be circumferentially distributed about longitudinal axis A to establish the pattern 348. Each aperture 344 may be circumferentially offset from an adjacent reference plane R1, R2 to establish a respective angle $\beta$ (indicated at $\beta$-1 to $\beta$-3). The angles $\beta$-1 to $\beta$-3 can differ such that the apertures 344 are non-uniformly distributed about the longitudinal axis A.

Figure 20A:
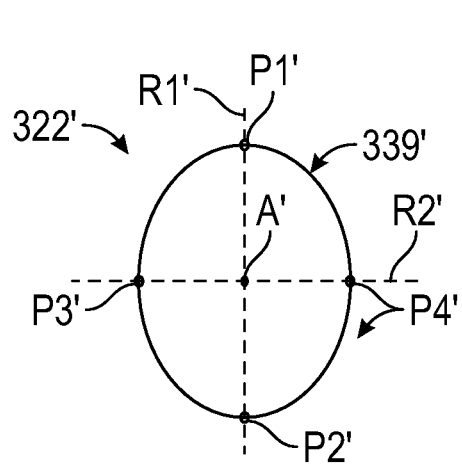
FIGS. 20A-20B illustrate exemplary baseplate profiles.
Figure 20B:
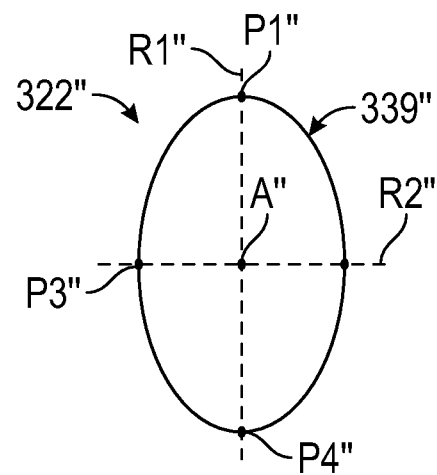

Other baseplate shapes or profiles can be utilized. In FIG. 20A, a perimeter 339' of baseplate 322' may have an elliptical, non-circular geometry established by points P1', P2' along a major axis and points P3', P4' along a minor axis of the ellipse. The major and minor axes can be aligned with first and second reference planes R1', R2', for example. In FIG. 20A, a perimeter 339" of baseplate 322" may have an ovoid-shaped geometry established by points P1', P2' along a major axis and points P3', P4' along a minor axis of the ovoid. The major and minor axes can be aligned with first and second reference planes R1", R2", for example.

Figure 21:
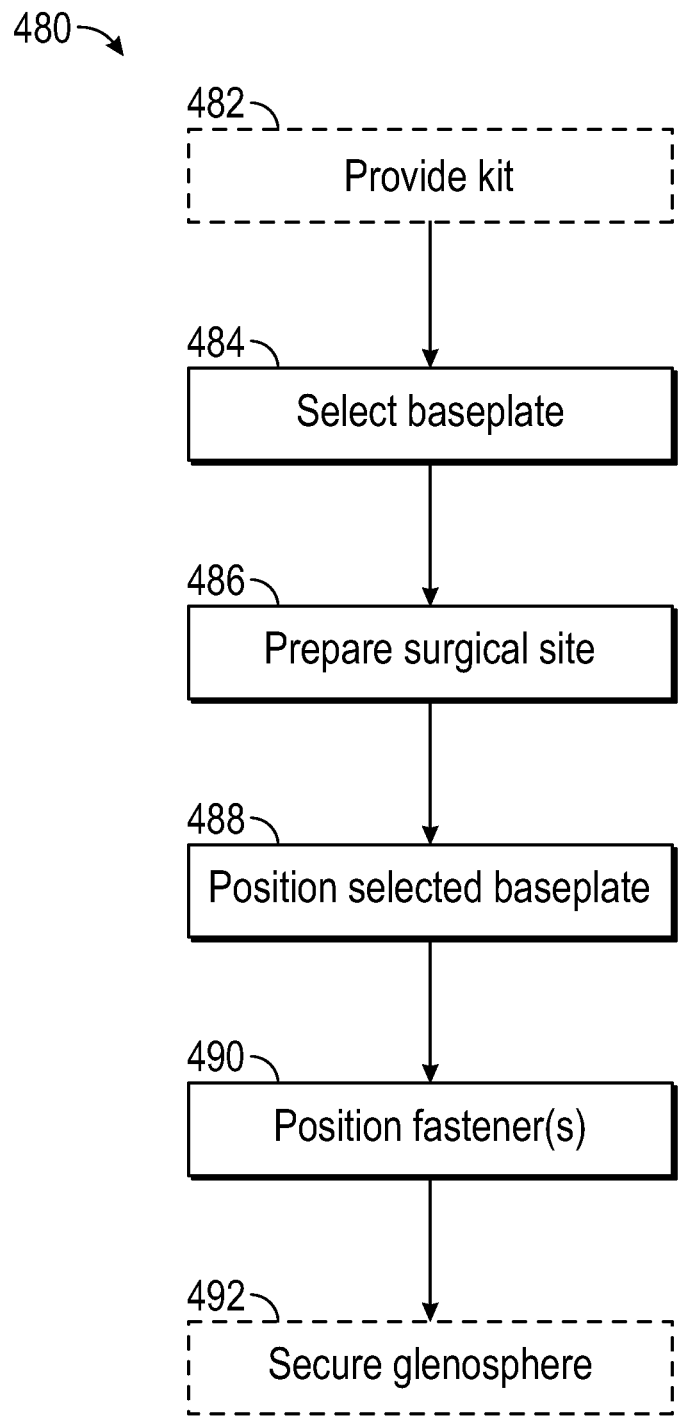
FIG. 21 illustrates an exemplary method of installing an orthopaedic implant at a surgical site.

FIG. 21 illustrates an exemplary method of installing an orthopaedic implant at a surgical site in a flowchart 480. The method may be utilized to perform an arthroplasty for restoring functionality to shoulders having advanced cartilage disease, such as repairing bone defects along a glenoid, for example. The method 480 can be utilized with any of the orthopedic implants, augment geometries and patterns of peripheral apertures disclosed herein. Fewer or additional steps than are recited below could be performed within the scope of this disclosure, and the recited order of steps is not intended to limit this disclosure.

Figure 23:
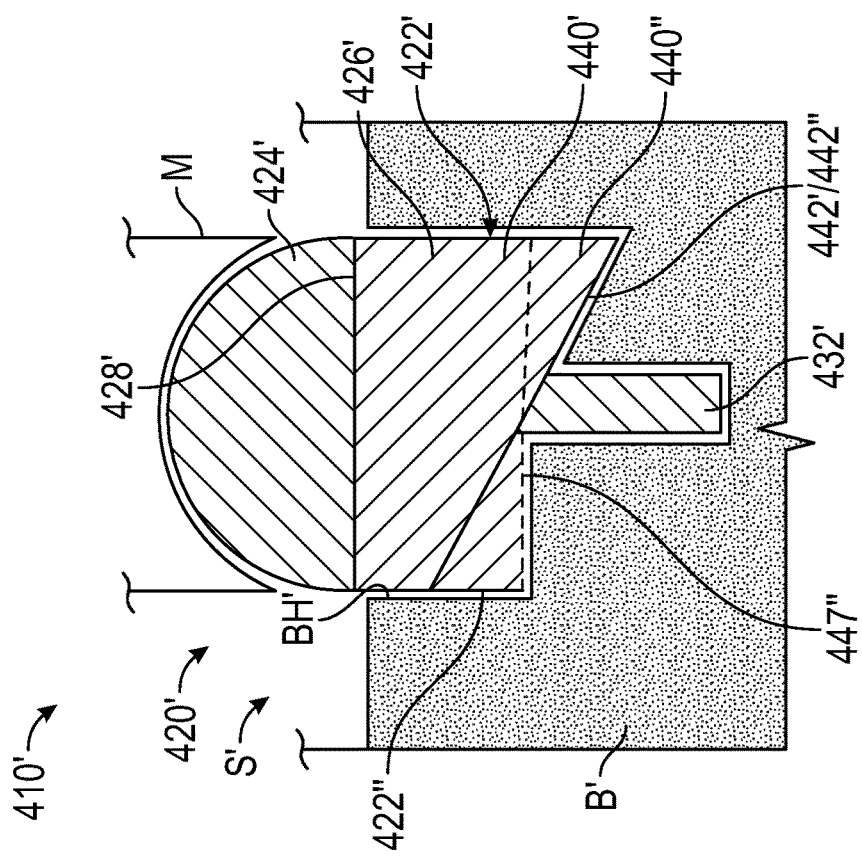
FIG. 23 illustrates an exemplary implant positioned at a surgical site.
Figure 22:
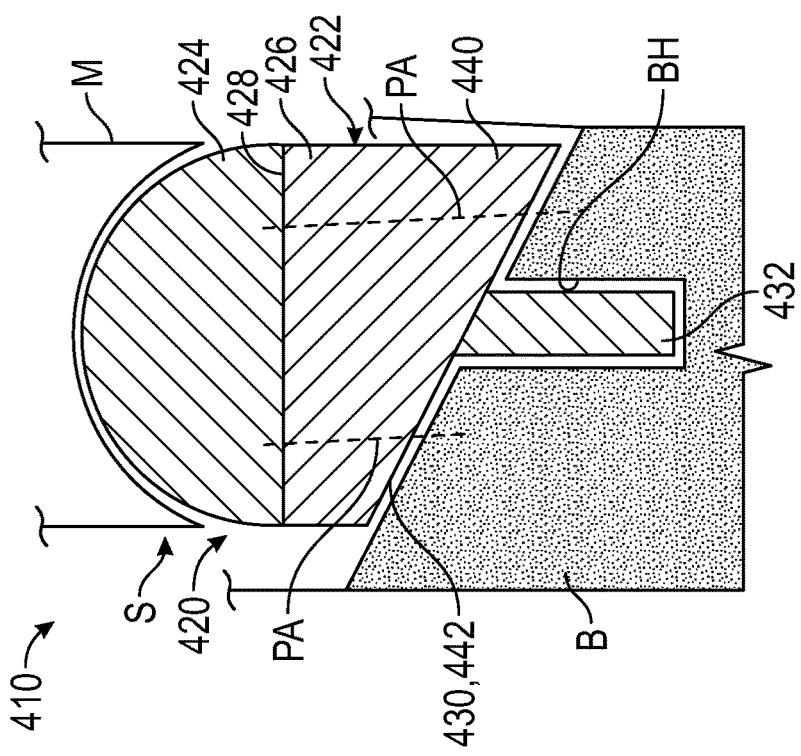
FIG. 22 illustrates an exemplary implant positioned at a surgical site.

A kit for arthroplasty can be provided at block 482. The kit can include any of the components disclosed herein including a set of baseplates, a plurality of peripheral fasteners, and one or more glenospheres. At step 484, a baseplate may be selected from a set of baseplates based on a surface profile of the surgical site. An exemplary surface profile of a surgical site S is illustrated by FIG. 22. Another exemplary surface profile of a surgical site S' is illustrated by FIG. 23. Other exemplary surface profiles of surgical sites S are disclosed in FIGS. 24A-24E and 25A-25E. The set of baseplates may include at least a first baseplate (e.g., baseplate 22) and a second baseplate (e.g., baseplate 122). Each of the baseplates can include peripheral apertures arranged to establish the respective pattern, including any of the patterns disclosed herein. The peripheral apertures of the second baseplate may be arranged to establish a second pattern (e.g., pattern 148) which may be circumferentially offset from a first pattern (e.g., pattern 48) of the first baseplate relative to longitudinal axis. The first and second pattern can have a common circumferential spacing between the respective peripheral apertures.

Referring to FIG. 22, with continuing reference to FIG. 21, the surgical site S can be prepared for receiving a prosthesis 410 including an implant 420 at step 486. The implant 420 can include a baseplate 422 and glenosphere 424. The implant 420 including the baseplate 422 may correspond to any of the implants and baseplates disclosed herein. A backside of the baseplate 422 can include an augment portion 440 which may be dimensioned to abut a surface and/or fill a bone void along the surgical site S. The augment portion 440 can have a generally wedge-shaped geometry.

One or more operations can be performed to prepare the surgical site S, such as one or more reaming, milling and drilling operations to establish a desired geometry of the surgical site. Step 486 can include forming a recess or bone hole BH at the surgical site S, such as an articulating surface of a glenoid, by removing tissue such as bone B at the surgical site S. A bone hole BH' may be formed to remove tissue from a defect in bone B' as illustrated by FIG. 23. The bone hole BH' can be dimensioned to at least partially receive at least an augment portion 440' of baseplate 422'. A defect in the glenoid can be characterized by the Walch Classification. The surgeon can measure bone loss utilizing imaging of the surgical site, such a radiogram or computed tomography technique, or can approximate a profile of the defect utilizing one or more sizers and/or measuring devices placed against the bone surface. The bone hole BH' can be dimensioned to approximate a profile of the defect. A baseplate 422" can be dimensioned such that an augment portion 440" may extend less than a full width of the baseplate 422" (shown in dashed lines in FIG. 23 for illustrative purposes).

At step 488, the selected baseplate 422 may be positioned relative to the surface profile and bone hole BH of the surgical site S. Step 488 can include positioning an anchoring stem 432 of the selected baseplate 422 in the bone hole BH to secure the baseplate 422 at the surgical site S.

At step 490, one or more fasteners may be positioned in a respective one of the peripheral apertures along respective passage axes PA (shown in dashed lines in FIG. 22 for illustrative purposes) to secure the selected baseplate to the surgical site S, as illustrated by the peripheral fasteners PF and peripheral apertures 44, 144 of the baseplates 22, 122 of FIGS. 24A-24E and 25A-25E. In FIGS. 24A-24E and 25A-25E, the peripheral fasteners PF may be compression screws that can serve to apply and maintain compression between the respective baseplate 22, 122 and glenoid surface which may reduce relative motion and may reduce tissue formation that may otherwise occur due to spacing between the contact surfaces of the baseplate and glenoid.

At step 492, a head portion or glenosphere 424 can be secured to the selected baseplate 422 which may provide an articulating surface for mating with an opposed articulating member M. The articulating member M can be an implant secured to a humerus, for example. The baseplate 422 may provide the articulating surface.

FIGS. 24A-24E illustrate the implant 20 situated relative to a surgical site S at different view angles. FIGS. 25A-25E illustrate the implant 120 situated relative to a surgical site S at different view angles. FIGS. 25A-25E can correspond to the same view angles of FIGS. 24A-24E, respectively. The geometry of the surgical sites S of FIGS. 24A-24E and 25A-25E may be the same or may differ. The implants 20, 120 of FIGS. 24A-24E and 25A-25E can be installed relative to the respective surgical site S utilizing the method 480 of FIG. 21, for example.

Each peripheral aperture 44, 144 may be dimensioned to receive a respective peripheral fastener PF to secure the plate body 26, 126 to the surgical site S. The peripheral fasteners PF may extend at least partially through a thickness of the bone tissue at the surgical site S.

In FIG. 24A, the baseplate 22 can be arranged such that the first and second reference planes R1, R2 may be substantially aligned with the Superior/Inferior (S/I) and/or Anterior/Posterior (A/P) planes of the patient. One or more of the peripheral apertures 44 and peripheral fasteners PF may be positioned along the S/I plane and/or A/P plane.

Figure 25C:
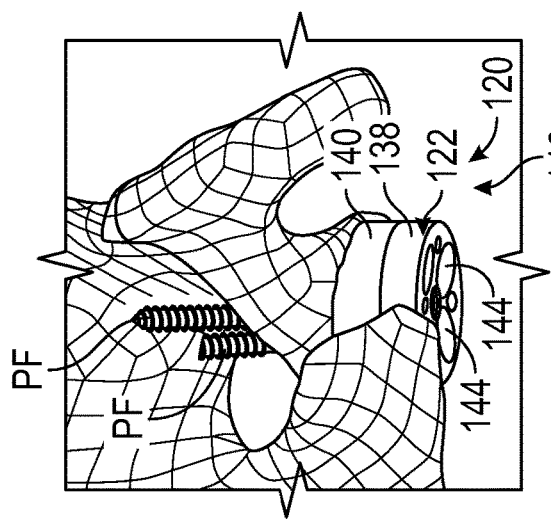
FIGS. 25A-25E illustrate the baseplate of FIG. 8 situated relative to a surgical site at different view angles.
Figure 25B:
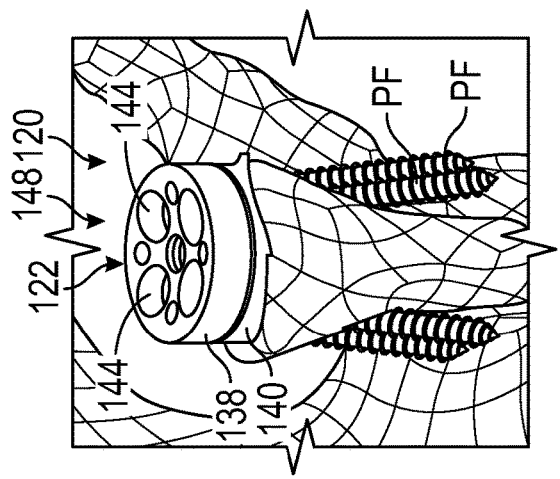
Figure 25A:
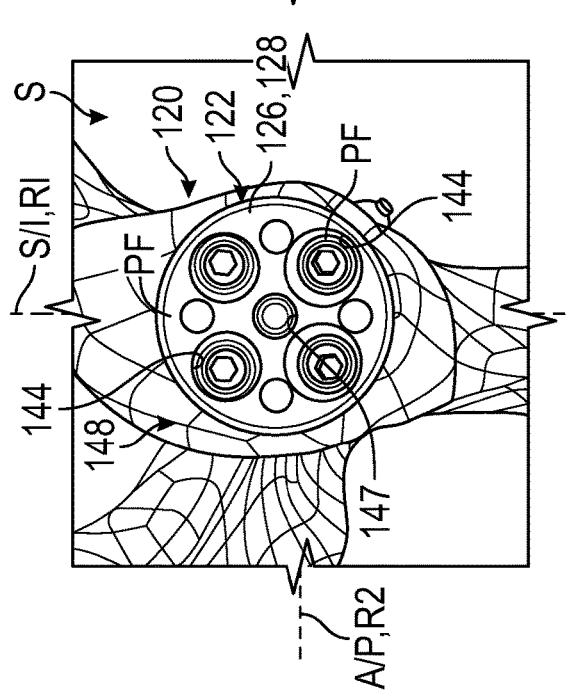
Figure 25E:
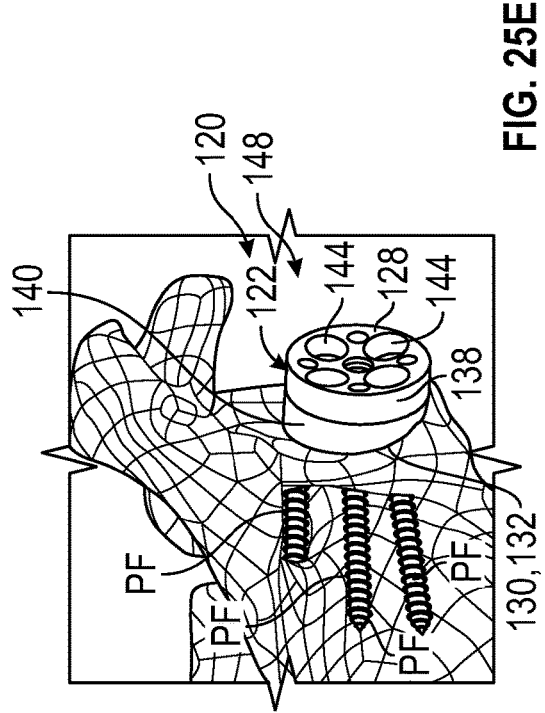
Figure 25D:
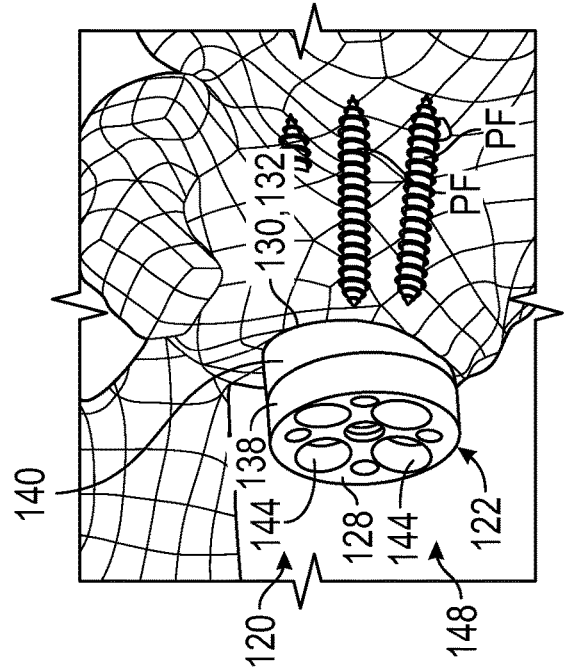

In FIG. 25A, the first reference plane R1 of the baseplate 122 may be arranged such that the first and second reference planes R1, R2 may be substantially aligned with the S/I and A/P planes. All of the peripheral apertures 144 can be circumferentially offset from the first reference plane R1, second reference plane R2, S/I plane, and/or A/P plane.

Figure 26:
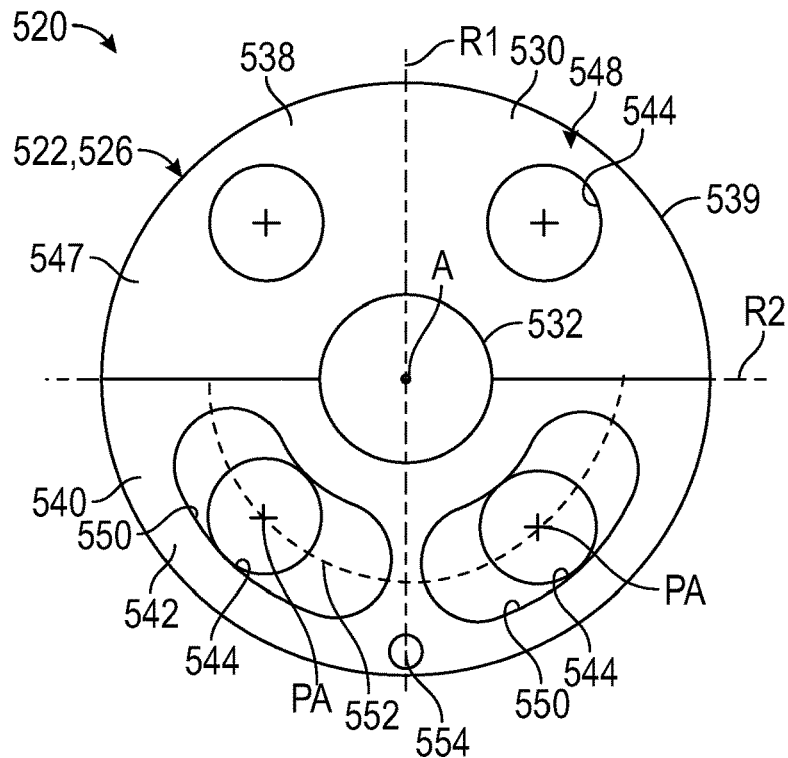
FIG. 26 illustrates a plan view of an exemplary orthopaedic implant including a baseplate having an augment portion in a first position.
Figure 27:
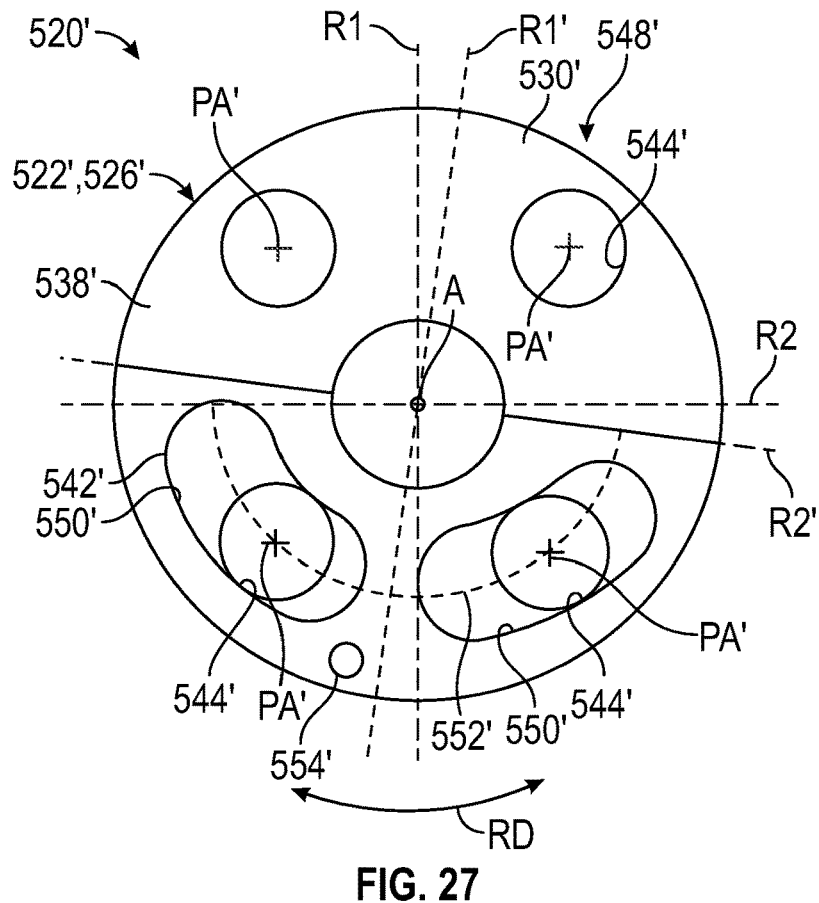
FIG. 27 illustrates the baseplate of FIG. 26 including the augment portion in a second position.

FIGS. 26-27 illustrate an exemplary orthopaedic implant 520. The implant 520 includes a baseplate 522 which may include a plate body 526 and an augment portion 540 positioned relative to a main body portion 538. The main body portion 538 and augment portion 540 may be separate and distinct components. The baseplate 522 may include a plurality of peripheral apertures 544 that may establish a pattern or layout 548. The apertures 544 can be arranged according to any of the patterns disclosed herein.

The augment portion 540 may include one or more channels 550 extending along a respective path 552. The channels 550 may be elongated slots and may be generally arcuate-shaped, as illustrated by FIGS. 26-27. A passage axis PA of a respective aperture 544 can be substantially aligned with the path 522 of a respective channel 550. A first reference plane R1 may bisect the augment portion 540, and a second reference plane R2 may be perpendicular to the first reference plane R2. The baseplate 522 can include a lock mechanism 554 which may be moveable between an unlocked mode and a locked mode. The lock mechanism 554 can include a retention pin that may selectively engage one or more depressions along the main body portion 538, for example.

The augment portion 540 may be rotatable in a direction RD (FIG. 27) about a longitudinal axis A of the baseplate 522 in the unlocked mode. The lock mechanism 554 can be moved to the locked mode which may limit movement of the augment portion 540 relative to the main body portion 538. FIG. 26 illustrates the augment portion 540 in a first position relative to the longitudinal axis A and peripheral apertures 544. FIG. 27 illustrates augment portion 540' in a second, different position relative to longitudinal axis A' and peripheral apertures 544'. As illustrated in FIG. 27, augment portion 540' may be positioned such that first and second reference planes R1', R2' established by the augment portion 540' may differ from a position of the first and second reference planes R1, R2 established by the augment portion 540 of FIG. 26. The channels 550 may be dimensioned to receive a respective fastener inserted through an adjacent peripheral aperture 544 at different positions relative to baseplate 522 such as different circumferential positions relative to the longitudinal axis A. The augment portion 540 may be positioned relative to the peripheral apertures 544 which may improve contact between the augment portion 540 and surface contour along a surgical site and may improve fixation of fasteners received in the respective apertures 544.

The novel implants and methods of this disclosure may provide versatility in securing the implants with fasteners to bone at a surgical site. The disclosed implants and augment geometries can be utilized to closely approximate a dimension of a bone surface, such as a bone void, which can lead to improved healing at the surgical site. The disclosed patterns of peripheral apertures can be utilized to improve fixation of the respective implant by selecting a pattern based on a geometry of the surgical site and bone thicknesses at the respective positions of the peripheral apertures. The disclosed baseplates can have a circular or non-circular geometry. The disclosed baseplates having substantially circular geometry may be utilized to orient the augment portion of the baseplate in a multitude of directions to establish a "best fit" for the augment portion, while ensuring that the peripheral screws may be in an optimal position.

Additionally, having multiple orientations of the augment portion may help preserve glenoid bone during the preparation for the baseplate.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure.

What is claimed is:

1. A method of installing an orthopaedic implant at a surgical site comprising:
    selecting a baseplate from a set of baseplates based on a surface profile of a surgical site;
    wherein each baseplate of the set of baseplates includes a plate body having a main body portion and a substantially wedge-shaped augment portion that cooperate to establish a front face and a rear face of the plate body, and a plurality of peripheral apertures extending between the front and rear faces, wherein a first reference plane extends along a longitudinal axis of the plate body to bisect the augment portion, the augment portion establishes an augment face section of the rear face, and the augment portion is dimensioned such that innermost and outermost points of the augment face section relative to the longitudinal axis are defined along the first reference plane;
    wherein the set of baseplates includes a first baseplate and a second baseplate, all of the peripheral apertures of the first baseplate arranged about the longitudinal axis establish a first pattern such that one or more of the peripheral apertures extend along the first reference plane, all of the peripheral apertures of the second baseplate arranged about the longitudinal axis are circumferentially offset from the first reference plane and establish a second pattern circumferentially offset from the first pattern, the circumferential offset measured by circumferential positions of the respective peripheral apertures in a clockwise direction from the outermost point relative to the longitudinal axis, the first and second patterns have a common circumferential spacing established and held between all of the respective peripheral apertures in both the first and second patterns, and all of the peripheral apertures that establish the respective first and second patterns are dimensioned to receive respective fasteners configured to secure the selected baseplate to bone;
    positioning the selected baseplate relative to the surface profile of the surgical site; and
    positioning a fastener in a respective one of the peripheral apertures to secure the selected baseplate to the surgical site.

2. The method as recited in claim 1, wherein:
    the plurality of peripheral apertures include a total of four peripheral apertures establishing the respective first and second patterns;
    a second reference plane extends along the longitudinal axis and is perpendicular to the first reference plane;
    two of the peripheral apertures of the first pattern are arranged along the first reference plane, and another two of the peripheral apertures of the first pattern are arranged along the second reference plane;
    the second pattern is established such that all of the peripheral apertures of the second baseplate are circumferentially offset from both the first and second reference planes.

3. The method as recited in claim 1, wherein an anchoring stem extends outwardly from the rear face along the longitudinal axis, and further comprising:
    positioning the anchoring stem in a bone hole along the surgical site; and
    securing a glenosphere to the selected baseplate, the glenosphere including an articulating surface having a generally convex geometry.

4. The method as recited in claim 1, wherein an anchoring stem extends outwardly from the rear face of the plate body.

5. The method as recited in claim 4, wherein the anchoring stem extends along the longitudinal axis.

6. The method as recited in claim 1, wherein a perimeter of the plate body is substantially circular.

7. The method as recited in claim 1, wherein the plurality of peripheral apertures of the respective first and second patterns are substantially equally distributed about the longitudinal axis.

8. The method as recited in claim 7, wherein the plurality of peripheral apertures include a total of four peripheral apertures establishing the respective first and second patterns.

9. The method as recited in claim 1, wherein a third reference plane extends along the longitudinal axis such that the first and third reference planes establish an acute angle, a pair of the peripheral apertures are circumferentially arranged along the third reference plane, and the acute angle is between 30 degrees and 60 degrees.

10. The method as recited in claim 9, wherein the plurality of peripheral apertures include a total of four peripheral apertures establishing the respective first and second patterns.

11. The method as recited in claim 10, wherein the four peripheral apertures are substantially uniformly distributed about the longitudinal axis.

12. The method as recited in claim 11, wherein the acute angle is approximately 45 degrees.

13. The method as recited in claim 1, wherein the plate body is releasably securable to a glenosphere, and the glenosphere includes an articulating surface having a generally convex geometry.

14. The method as recited in claim 13, wherein the glenosphere includes a recess dimensioned to at least partially receive the main body portion of the plate body.

15. The method as recited in claim 14, wherein a perimeter of the main body portion of the plate body is dimensioned to cooperate with a perimeter of the recess to establish a Morse taper connection.

16. The method as recited in claim 1, wherein a second reference plane extends along the longitudinal axis and is perpendicular to the first reference plane, and the second pattern is established such that all of the peripheral apertures of the second baseplate are circumferentially offset from the second reference plane.

17. The method as recited in claim 16, wherein a perimeter of the plate body is substantially circular.

18. The method as recited in claim 17, wherein the plurality of peripheral apertures that establish the respective first and second patterns are substantially equally distributed about the longitudinal axis.

19. The method as recited in claim 17, wherein one or more of the peripheral apertures that establish the respective first and second patterns extend between the front face and a position along the rear face established by the augment portion.

20. The method as recited in claim 19, wherein:
the plurality of peripheral apertures that establish the respective first and second patterns are a total of four peripheral apertures substantially equally distributed about the longitudinal axis; and
a third reference plane extends along the longitudinal axis such that the first and third reference planes establish an acute angle, a pair of the peripheral apertures of the second pattern are circumferentially arranged along the third reference plane, and the acute angle is between 30 degrees and 60 degrees.

21. The method as recited in claim 1, wherein the step of positioning the selected baseplate relative to the surface profile of the surgical site includes arranging the selected baseplate such that the first reference plane is substantially aligned with a Superior/Inferior plane of a patient.

22. The method as recited in claim 21, wherein the selected baseplate is the second baseplate.

23. The method as recited in claim 22, wherein a perimeter of the plate body is substantially circular.

24. The method as recited in claim 23, wherein:
an anchoring stem extends along the longitudinal axis and outwardly from the rear face of the plate body;
a second reference plane extends along the longitudinal axis and is perpendicular to the first reference plane;
the plurality of peripheral apertures that establish the respective first and second patterns are substantially equally distributed about the longitudinal axis; and
the second pattern is established such that all of the peripheral apertures of the second baseplate are circumferentially offset from the second reference plane.

25. The method as recited in claim 24, wherein:
the plurality of peripheral apertures that establish the respective first and second patterns are a total of four peripheral apertures; and
the first and second patterns are established such that one or more of the respective peripheral apertures extend between the front face and a position along the rear face established by the augment portion.

* * * * *